United States Patent
Lee et al.

(10) Patent No.: US 8,221,995 B2
(45) Date of Patent: Jul. 17, 2012

(54) METHODS AND COMPOSITIONS FOR DIAGNOSIS AND/OR PROGNOSIS IN SYSTEMIC INFLAMMATORY RESPONSE SYNDROMES

(76) Inventors: Seok-Won Lee, San Diego, CA (US); Kelline M. Rodems, Oceanside, CA (US); David W. Oelschlager, San Diego, CA (US); Uday Kumar Veeramallu, San Diego, CA (US); Joseph A. Buechler, Carlsbad, CA (US); Paul H. McPherson, Encinitas, CA (US)

( * ) Notice: Subject to any disclaimer, the term of this patent is extended or adjusted under 35 U.S.C. 154(b) by 0 days.

(21) Appl. No.: 12/663,841

(22) PCT Filed: Jun. 27, 2008

(86) PCT No.: PCT/US2008/068667
§ 371 (c)(1),
(2), (4) Date: May 21, 2010

(87) PCT Pub. No.: WO2009/006347
PCT Pub. Date: Jan. 8, 2009

(65) Prior Publication Data
US 2010/0240078 A1    Sep. 23, 2010

(51) Int. Cl.
*G01N 33/00* (2006.01)
(52) U.S. Cl. .................................. 435/7.94
(58) Field of Classification Search .............. None
See application file for complete search history.

(56) References Cited

U.S. PATENT DOCUMENTS

| | | |
|---|---|---|
| 4,531,936 A | 7/1985 | Gordon |
| 5,453,359 A | 9/1995 | Gargan et al. |
| 5,480,792 A | 1/1996 | Buechler et al. |
| 5,525,524 A | 6/1996 | Buechler et al. |
| 5,571,698 A | 11/1996 | Ladner et al. |
| 5,631,171 A | 5/1997 | Sandstrom et al. |
| 5,639,617 A | 6/1997 | Bohuon |
| 5,679,526 A | 10/1997 | Buechler et al. |
| 5,710,008 A | 1/1998 | Jackowski |
| 5,824,799 A | 10/1998 | Buechler et al. |
| 5,843,690 A | 12/1998 | Gargan et al. |
| 5,851,776 A | 12/1998 | Valkirs |
| 5,874,211 A | 2/1999 | Bandman et al. |
| 5,885,527 A | 3/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,965,375 A | 10/1999 | Valkirs |
| 5,985,579 A | 11/1999 | Buechler et al. |
| 6,001,606 A | 12/1999 | Ruben et al. |
| 6,019,944 A | 2/2000 | Buechler |
| 6,051,697 A | 4/2000 | Bandman et al. |
| 6,057,098 A | 5/2000 | Buechler et al. |
| 6,113,855 A | 9/2000 | Buechler |
| 6,143,576 A | 11/2000 | Buechler |
| 6,190,872 B1 | 2/2001 | Slotman |
| 6,207,395 B1 | 3/2001 | Valkirs et al. |
| 6,303,321 B1 | 10/2001 | Tracey et al. |
| 6,451,562 B1 | 9/2002 | Ruben et al. |
| 6,488,925 B2 | 12/2002 | Ruben et al. |
| 6,495,129 B1 | 12/2002 | Li et al. |
| 6,503,722 B1 | 1/2003 | Valkirs |
| 6,623,942 B2 | 9/2003 | Ruben et al. |
| 6,673,562 B2 | 1/2004 | Shi |
| 6,730,480 B1 | 5/2004 | Pitson et al. |
| 6,743,595 B1 | 6/2004 | Gosselin et al. |
| 6,811,773 B1 | 11/2004 | Gentz et al. |
| 6,828,110 B2 | 12/2004 | Lee et al. |
| 6,849,413 B2 | 2/2005 | Young et al. |
| 6,908,739 B2 | 6/2005 | Buechler et al. |
| 7,041,460 B2 | 5/2006 | Gentz et al. |
| 7,052,858 B2 | 5/2006 | Gray et al. |
| 7,329,738 B1 | 2/2008 | Lee et al. |
| 7,358,055 B2 | 4/2008 | Valkirs et al. |
| 7,361,473 B2 | 4/2008 | Valkirs et al. |
| 7,364,865 B2 | 4/2008 | Gentz et al. |
| 7,374,888 B2 | 5/2008 | Valkirs et al. |
| 7,393,647 B2 | 7/2008 | Valkirs et al. |
| 7,572,600 B2 | 8/2009 | Berahovich et al. |
| 7,582,416 B2 | 9/2009 | Migeotte et al. |
| 7,659,251 B2 | 2/2010 | Migeotte et al. |
| 2002/0061551 A1 | 5/2002 | Ruben et al. |
| 2002/0076746 A1 | 6/2002 | Ruben et al. |
| 2003/0096260 A1* | 5/2003 | Miao et al. .................. 435/6 |

(Continued)

FOREIGN PATENT DOCUMENTS

EP    0099947 A1    2/1984
(Continued)

OTHER PUBLICATIONS

Aggarwal, et al. Evaluation of Serum Lipid Profile and Cardiac Enzyme Changes in Cerebrovascular Accidents. J. Indian Med. Assoc. 1995;93:331-332. Akiyama, et al. Changes in Serum Concentrationsn of Matrix Metalloproteinases, Tissue Inhibitors of Metalloproteinases and Type IV Collagen in Patients with Various Types of Glomerulonephritis. Res. Commun. Mol. Pathol. Pharmacol. 1997;95:115-128.
Albrechtsen, et al. Quantification of Glial Fibrillary Acidic Protein (GFAP) in Human Body Fluids by means of ELISA Employing a Monoclonal Antibody. Neuroimmunol. 1985;8:301-309.
Amaro, et al. Plasma leukocyte elastase concentration in angiographically diagnosed coronary artery disease. Eur. Heart J. 1995;16:615-622.
Anderson, L. Candidate Based Proteomics in the Search for Biomarkers of Cardiovascular Disease. J Physiology 563.1. 2004; 23-60.
Angus, et al. Epidemiology of severe sepsis in United states: Analysis of incidence, outcome, and associated costs of care. Crit. Care Med. 2001;29:1303-10.
Ardissino, et al. Tissue Factor antigen and activity in human coronary atherosclerotic plaques. Lancet 1997;349:769-771.
Asai, et al. Absence of procarboxypeptidase R induces complement-mediated lethal inflammation in lipopolysaccharide-primed mice. J Immunol. Oct. 1, 2004;173(7):4669-74.

(Continued)

*Primary Examiner* — Cherie M Woodward
(74) *Attorney, Agent, or Firm* — Wilson Sonsini Goodrich & Rosati

(57) ABSTRACT

The present invention relates to methods and compositions for diagnosing SIRS, sepsis, severe sepsis, septic shock, or MODS in a subject, or assigning a prognostic risk for one or more clinical outcomes for a subject suffering from SIRS, sepsis, severe sepsis, septic shock, or MODS, the method comprising performing an immunoassay for CCL23 splice variant.

4 Claims, No Drawings

U.S. PATENT DOCUMENTS

| | | | |
|---|---|---|---|
| 2003/0109420 A1 | 6/2003 | Valkirs et al. | |
| 2003/0114379 A1 | 6/2003 | Li et al. | |
| 2003/0147846 A1 | 8/2003 | Ruben et al. | |
| 2003/0215460 A1 | 11/2003 | Schall et al. | |
| 2004/0097460 A1* | 5/2004 | Ivey et al. ............ | 514/44 |
| 2004/0106142 A1 | 6/2004 | Ivey et al. | |
| 2004/0121343 A1 | 6/2004 | Buechler et al. | |
| 2004/0121350 A1 | 6/2004 | Anderberg et al. | |
| 2004/0126767 A1 | 7/2004 | Anderberg et al. | |
| 2004/0152169 A1 | 8/2004 | Gentz et al. | |
| 2004/0191255 A1 | 9/2004 | Lillard et al. | |
| 2004/0203083 A1 | 10/2004 | Buechler et al. | |
| 2004/0219603 A1 | 11/2004 | Devarajan et al. | |
| 2004/0236092 A1 | 11/2004 | Dziarski et al. | |
| 2004/0253637 A1 | 12/2004 | Buechler et al. | |
| 2004/0260058 A1 | 12/2004 | Scheek et al. | |
| 2005/0069540 A1 | 3/2005 | Liu et al. | |
| 2005/0148029 A1 | 7/2005 | Buechler et al. | |
| 2005/0164238 A1* | 7/2005 | Valkirs et al. ............ | 435/6 |
| 2005/0181386 A1 | 8/2005 | Diamond et al. | |
| 2005/0196817 A1 | 9/2005 | Kingsmore et al. | |
| 2005/0214826 A1 | 9/2005 | Mor et al. | |
| 2005/0255484 A1 | 11/2005 | Valkirs et al. | |
| 2006/0034863 A1 | 2/2006 | Schall et al. | |
| 2006/0063223 A1* | 3/2006 | Berahovich et al. ............ | 435/23 |
| 2006/0078559 A1 | 4/2006 | Migeotte et al. | |
| 2006/0228359 A1 | 10/2006 | Gentz et al. | |
| 2007/0083334 A1 | 4/2007 | Mintz et al. | |
| 2007/0087986 A1 | 4/2007 | Premack et al. | |
| 2007/0092911 A1* | 4/2007 | Buechler et al. ............ | 435/7.1 |
| 2007/0172906 A1 | 7/2007 | Valkirs et al. | |
| 2007/0218498 A1 | 9/2007 | Buechler et al. | |
| 2008/0050832 A1 | 2/2008 | Buechler et al. | |
| 2008/0274109 A1 | 11/2008 | Gentz et al. | |
| 2009/0004755 A1 | 1/2009 | Lee et al. | |
| 2009/0053739 A1 | 2/2009 | Migeotte et al. | |
| 2010/0009406 A1 | 1/2010 | Migeotte et al. | |

FOREIGN PATENT DOCUMENTS

| | | |
|---|---|---|
| EP | 1607745 A2 | 12/2005 |
| EP | 1666881 A2 | 6/2006 |
| EP | 1607745 A3 | 7/2006 |
| EP | 1666881 A3 | 9/2007 |
| EP | 2020604 A1 | 2/2009 |
| JP | 2007274986 | 10/2007 |
| WO | WO 96/32481 A1 | 10/1996 |
| WO | WO 98/14582 A1 | 4/1998 |
| WO | WO 01/26676 A1 | 4/2001 |
| WO | WO 01/63280 A2 | 8/2001 |
| WO | WO 02/089657 A2 | 11/2002 |
| WO | WO 01/63280 A3 | 1/2003 |
| WO | WO 02/089657 A3 | 2/2003 |
| WO | WO 03/016910 A1 | 2/2003 |
| WO | WO 03/031603 A1 | 4/2003 |
| WO | WO 03/073099 A1 | 9/2003 |
| WO | WO 03/084388 A2 | 10/2003 |
| WO | WO 03/096017 A1 | 11/2003 |
| WO | WO 2004/043236 A2 | 5/2004 |
| WO | WO 2004/044555 A2 | 5/2004 |
| WO | WO 2004/058055 A2 | 7/2004 |
| WO | WO 2004/059293 A2 | 7/2004 |
| WO | WO 03/084388 A3 | 8/2004 |
| WO | WO 2004/044555 A3 | 9/2004 |
| WO | WO 2004/087949 A2 | 10/2004 |
| WO | WO 2004/059293 A3 | 3/2005 |
| WO | WO 2004/058055 A3 | 4/2005 |
| WO | WO 2005/033327 A2 | 4/2005 |
| WO | WO 2005/048823 A2 | 6/2005 |
| WO | WO 2004/043236 A3 | 7/2005 |
| WO | WO 2005/048823 A3 | 11/2005 |
| WO | WO 2005/033327 A3 | 8/2006 |
| WO | WO 2006/135382 A2 | 12/2006 |
| WO | WO 2006/135382 A3 | 12/2007 |
| WO | WO 2009/006347 A2 | 1/2009 |
| WO | WO 2009/006347 A3 | 4/2009 |

OTHER PUBLICATIONS

Austgulen, et al. Increased maternal plasma levels of soluble adhesion molecules (ICAM-1, VCAM-1, E-selectin) in preeclampsia. Eur. J. Obstet. Gynecol. Reprod. Biol. 1997;71:53-58.

Badr-Eldin, et al. Eosinophil cationic protein as a serological marker of disease activity in childhood bronchial asthma. East Mediterr. Health J. 1999;5:664-75.

Baker, et al. Serum Metalioproteinases and their inhibitors: markers for malignant potential Br. J. Cancer 1994;70:506-512.

Balagopalakrishna, et al. Modification of Low Density Lipoproteins by Erythrocytes and Hemoglobin Under Hypoxic Conditions. Adv. Exp. Med. Biol. 1997;411:337-345.

Balcli, et al. Usefulness of procalcitonin for diagnosis of sepsis in the intensive care unit. Crit Care. Feb. 2003;7(1):85-90.

Bandoh, et al. Sequential changes of Kl-6 in sera of patients with interstitial pneumonia associated with polymyositis/dermatomyositis. Ann. Rheum. Dis. 2000;59: 257-62.

Banks, et al. Circulating intercellular adhesion molecule-1 (1CAM-1), E-selectin and vascular cell adhesion molecule-1 (VCAM-1) in human malignancies. Br. J. Cancer 1993;68:122-124.

Bates, et al. Neurotrophin-3 Promates Cell Death Induced in Cerebral lschemia, Oxygen-Glucose Deprivation, and Oxidative Stress: Possible Involvement of Oxygen Free Radicals. Neurobiol. Dis. 2002;9:24-37.

Bazzan, et al. No evidence of platelet activation during atrial pacing in subjects with stable angina. Cardiologia 1989;34, 217-220.

Becker et al. Procalcitonin and the calcitonin gene family of peptides in inflammation, infection, and sepsis: A journey from calcitonin back to its precursors. J. clin. endocrinol. Metab. 2004;89(4): 1512-1525.

Bialik, et al. Myocyte Apoptosis during Acute Myocardial Infarction in the Mouse Localizes to Hypoxic Regions but Occurs Independently of p53. J. Clin. Invest. 1997;100:1363-1372.

Biasucci, et al. Elevated Levels of lnterleukin-6 in Unstable Angina. Circulation 1996;94:874-877.

Biasucci, et al. Episodic Activation of the Coagulation System in Unstable Angina Does Not Elicit an Acute Phase Reaction. Am. J. Cardiol. 1996;77:85-87.

Biasucci, et al. Increasing Levels of lnterieukin (IL)-1Ra and IL-6 During the First 2 Days of Hospitalization in Unstable Angina Are Associated With Increased Risk of In-Hospital Coronary Events. Circulation 1999;99:2079-2084.

Biasucci, et al. Temporal Relation Between lschemic Episodes and Activation of the Coagulation System in Unstable Angina. Circulation 1996;93:2121-2127.

Biasucci, L.M. CDC/AHA Workshop on Markers of Inflammation and Cardiovascular Disease.Circulation. 2004;110:e560-e567.

Bitsch, et al. A Longitudinal Prospective Study of Soluble Adhesion Molecules in Acute Stroke. Stroke 1998;29:2129-2135.

Blankaert, et al. Constitutive Release of Metalloproteinase-9 (92-kd Type IV Collagenase) by Kaposi's Sarcoma Cells. J. Acquir. Immune Defic. Syndr. Hum. Retrovirol. 1998;18:203-209.

Blann, et al. Evidence of platelet activation in hypertension. J. Hum. Hypertens. 1997;11:607-609.

Blann, et al. Soluble P-selectin in Atherosclerosis: A Comparison with Endothelial Cell and Platelet markers. Thromb. Haemost. 1997;77:1077-1 080.

Bollensen, et al. Adenylate kinase enzyme activity in cases of brain infarction. Acta Neurol Scand 1989;79:53-582.

Bone, et al. Definitions for sepsis and organ failure and guidelines for the use of innovative therapies in sepsis. Chest 1992;101:1644-53.

Bonfrer, et al. The luminescence immunoassay S-100: a sensitive test to measure circulating S-100B its prognostic value in malignant melanoma. Br. J. Cancer 1998;77:2210-2214.

Bonomini, et al. Serum Levels of Soluble Adhesion Molecules in Chronic Renal Failure and Dialysis Patients. Nephron 1998;79:399-407.

Bonow, New insights Into the Cardiac Natriuretic Peptides. Circulation 1996;93:1946-1950.

Bossink, et al. Plasma Levels of the Chemokines Monocyte Chemotactic Proteins-1 and -2 Are Elevated in Human Sepsis. Blood 1995;86:3841-3847.

Bossink, et al. Prediction of Mortality in Febrile Medical Patients. Chest 1998;113:1533-41.

Bousquet, et al. Eosinophillic Inflammation in Asthma. New Engl. J. Med. 1990;323: 1033-9.

Bowen-Pope, et al. Platelet-Derived Growth Factor in Vivo: Level, Activity, and Rate of Clearance. Blood 1984;64:458-469.

Brooks, et al. Identification of amino acid residues in the C-terminal tail of big endothelin-1 involved in processing to endothelin-1. J. Mol. Endocrinol. 1998;21:307-15.

Brown, et al. Identification of 92-kD Gelatinase in Human Coronary Atherosclerotic Lesions. Circulation 1995;91:2125-2131.

Bruccoleri, et al. Brain Natriuretic Peptide in Patients With Acute Myocardial Infarction and Hypertension. Abstract No. H059. Clinical Chemistry and Laboratory Medicine, Abstracts Volume. Poster Abstracts—IFCC-WorldLab '99—Frienze, Jun. 6-11, 1999: S 440.

Brunkhorst, et al. Procalcitonin for Early Diagnosis and Differentiation of SIRS, Sepsis, Severe Sepsis, and Septic Shock. Intensive Care Med. 2000; 26:S148-S152.

Carlstedt, et al. Proinflammatory cytokines, measured in a mixed population on arrival in the emergency department, are related to mortality and severity of disease. J. Intern. Med. 1997;242:361-365.

Carraro, et al. Apoptosis of skeletal and cardiac muscles and physical exercise. Aging (Milano) 1997;9:19-34.

Carter, et al. Platelet GP IIa Pia and GP Ib Variable Number Tandem Repeat Polymorphisms and Markers of Platelet Activation in Acute Stroke. Arterioscler. Thromb. Vasc. Biol. 1998;18:1124-1131.

Carter, et al. Purification, cloning, expression and biological characterization of an interleukin-1 receptor antagonist protein. Nature 1990;344:633-638.

Carville, et al. Thrombus precursor protein (TpPTM): marker of thrombosis early in the pathogenesis of myocardial infarction. Clin. Chem. 1996;42:1537-1541.

Charpentier, et al. Brain natriuretic peptide: A marker of myocardial dysfunction and prognosis during severe sepsis. Crit Care Med. Mar. 2004;32(3):660-5.

Chinnaiyan, et al. Short Communication Molecular signatures of sepsis: Multiorgan gene expression profiles of systemic inflammation. Am J Pathol. Oct. 2001;159(4):1199-1209.

Chong, et al. Plasma P-Selectin Is Increased in Thrombotic Consumptive Platelet Disorders. Blood 1994;83:1535-1541.

Chua, et al. Marked elevations in N-terminal brain natriuretic peptide levels in septic shock. Critical Care. 2004;8:R248-R250.

Cohen, et al. Plasma Clearance and Tissue Distribution of Recombinant Human Platelet-Derived Growth Factor (B-Chain Homodimer) in Rats. J. Surg. Res. 1990;49:447-452.

Crouch, et al. Surfactant protein-D and pulmonary host defense. Respir. Res, 2000;1:93-108.

Cwirla, et al. Peptides on Phage: A vast library of peptides for identifying ligands. Proc. Natl. Acad. Sci. USA 1990;87, 6378-82.

Davi, et al. Increased Levels of Soluble P-selectin in Hypercholesterolemic Patients. Circulation 1998;97:953-957.

Davidson, et al. C-Type Natriuretic Peptide. Circulation 1996;93:1155-9.

Davie, et al. The Coagulation Cascade: Initiation, Maintenance, and Regulation. Biochem. 1991;30:10363-10370.

De Caterina, et al. Platelet activation in angina at rest. Evidence by paired measurement of plasma beta-thromboglobulin and platelet factor 4*. Eur. Heart J. 1988;9:913-922.

De Rose, et al. Circulating Adhesion Molecules in Cystic Fibrosis. Am. J. Respir. Crit. Care Med. 1998;157:1234-1239.

Delogu, et al. Serum neopterin and soluble interleukin-2 receptor for prediction of a shock state in gram-negative sepsis. J Crit Care. Jun. 1995;10(2):64-71.

Depre, et al. Expression of inducible nitric oxide synthase in human coronary atherosclerotic plaque. Cardiovasc. Res. 1999;41:465-472.

Devlin, et al. Random Peptide Libraries: A source of Specific Protein Binding Molecules. Science 1990;249, 404-6.

Dinerman, et al. Increased Neutrophil Elastase Release in Unstable Angina Pectoris and Acute Myocardial Infarction. J. Am. Coil. Cardiol. 1990;15:1559-1563.

Dobosz, et al. Immunochemical Analysis of Some Proteins in Cerebrospinal Fluid and Serum of Patients with Ischemic Strokes. Folia Neuropathol. 1994;32:129-137.

Doellner, et al. Increased serum concentrations of soluble tumor necrosis factor receptors p55 and p75 in early onset neonatal sepsis. Early Human Development. Oct. 1, 1998;52(3)251-261.

Dollner, et al. Inflammatory mediators in umbilical plasma from neonates who develop early-onset sepsis. Biol Neonate. Jul. 2001;80:41-7-2404 PCT/US2004031769.

Dunlop, et al. Characterization of GMP-140 (P-selectin) as a Circulating Plasma Protein. J. Exp. Med. 1992;175:1147-1150.

Egermayer, et al. Usefulness of D-dimer, blood gas, and respiratory rate measurements for excluding pulmonary embolism. Thorax 1998;53:830-34.

Eisenberg, et al. Interleukin 1 receptor antagonist is a member of the interleukin 1 gene family: Evolution of a cytokine control mechanism. Proc. Natl. Acad. Sci. U. S. A. 1991;88:5232-5236.

Emsley, et al. Crystal Structure of the von Willebrand Factor Al Domain and Implications for the Binding of Platelet Glycoprotein Ib*. J. Biol. Chem. 1998;273:10396-10401.

Endo, et al. Elevated Levels of Serum and Plasma Metalloproteinases in Patients with Gastric Cancer. Anticancer Res. 1997;17:2253-2258.

Endo, et al. Plasma Interleukin 8 and Polymorphonuclear Leukocyte Elastase Concentrations in Patients with Septic Shock, J. Inflamm. 1995;45:136-142.

Eriksson, et aL Leukocyte Elastase as a Marker in the Diagnosis of Acute Appendicitis. Eur. J. Surg. 1995;161:901-905.

Ertenli, et al. P-Selectin as a Circulating Molecular marker in Rheumatoid Arthritis with Thrombocytosis. J. Rheumatol. 1998;25:1054-1058.

Estrada, et al. High Plasma level of Endothelin-1 and Atrial Natriuretic peptide in Patients with Acute Ischemic Stroke. Am. J. Hypertens. 1994;7:1085-9.

European search report dated Feb. 10, 2010 for Application No. 06816195.9.

European search report dated Jul. 13, 2010 for Application No. 08772206.2.

Falciani, et al. Elevated Tissue Factor and Tissue Factor Pathway Inhibitor Circulating Levels in Ischaemic Heart Disease Patients. Thromb. Haemost. 1998;79:495-499.

Fassbender, et al. Changes in coagulation and fibrinolysis markers in acute ischemic stroke treated with recombinant tissue plasminogen activator. Stroke. Oct. 1999;30(10):2101-4.

Felker, et al. Natriuretic peptides in the diagnosis and management of heart failure. CMAJ. Sep. 12, 1996;175(6):611-617.

Fischer, et al. Evaluation of a New, Rapid Bedside Test for Quantitative Determination of B-Type Natriuretic Peptide. Intensive Care Med. 2003;29:1043-51.

Fischer, et al. Serum concentrations and peripheral secretion of the beta chemokines monocyte chemoattractant protein 1 and macrophage inflammatory protein 1a in alcoholic liver disease. Gut 1999;45:416-420.

Forssmann, et al. The endocrine heart and natriuretic peptides: histochemistry, cell biology, and functional aspects of the renal urodilatin system. Histochem Cell Biol 1998);110:335-357.

Fox, Shedding of adhesion receptors from the surface of activated platelets. Blood Coagul. Fibrinolysis 1994;5:291-304.

Freitag, et al. Plasma Brain Natriuretic Peptide Levels and Blood Pressure Tracking in the Framingham Heart Study. Hypertension. 2003;41:978-983.

Freyburger, et al. Flow cytometry assessment of leukocyte functions in vascular pathologies. Hematol Cell Ther. Dec. 1996;38:513-526.

Frijns, et al. Soluble Adhesion Molecules Reflect Endothelial Cell Activation in Ischemic Stroke and in Carotid Atherosclerosis. Stroke 1997;8:2214-2218.

Fujiwara et al. Synthesis of Human C-Type Natriuretic Peptide 22 Using Chiorotrityl Resin and Tetrflouroboric Acid Deprotection. Chem. Pharm. Bull. (Tokyo) 1996;44:1326-31.

Gabay, et al. Interleukin 1 Receptor Antagonist (IL-1Ra) Is an Acute-Phase Protein J. Clin. Invest. 1997; 99(12):2930-2940.

Gallino, et al. Fibrin formation and platelet aggregation in patients with acute myocardial infarction: Effects on intravenous and subcutaneous low-dose heparin. Am. Heart J. 1986;112:285-290.

Gamble, et al. Prevention of Activated Neutrophil Adhesion to Endothelium by Soluble Protein GMP14O. Science 1990;249:414-417.

Gando, et al. Combined activation of coagulation and inflammation has an important role in multiple organ dysfunction and poor outcome after severe trauma. Thromb Haemost. 2002; 88(6): 943-9.
Gando, et al. Increased Neutrophil Eastase, Persistent ntravascular Coagulation, and Decreased Fibrinolytic Activity in Patients with Posttraumatic Acute Respiratory Distress Syndrome. J Trauma 1997;42:1068-1072.
Garbisa, et al. Correlation of Serum Metalloproteinase Levels with Lung Cancer Metastasis and Response to Therapy. Cancer Res. 1992;52:4548-4549.
Genereau, et al. Human Neutrophil Elastase in Temporal (Giant Cell) Arteritis: Plasma and Immunohistochemical Studies. J. Rheumatol. 1998;25:710-713.
Gensini, et al. Increased Protein C and Fibrinopeptide a Concentration in Patients with Angina. Thromb. Res. 1988;50:517-525.
George, et al. Evidence for altered hepatic matrix degradation in genetic haemochromatosis. Gut 1998;42:715-720.
Ghaisas, et al. Elevated Levels of Circulating Soluble Adhesion Molecules in Peripheral Blood of Patients wiith Unstable Angina. Am. J. Cardiol. 1997;80:617-619.
Ghanem, et al. Increased low density lipoprotein oxidation in stable kidney transplant recipients. Kidney Int. 1996;49:488-493.
Giamarellos-Bourboulis, et al. Procalcitonin: a marker to clearly differentiate systemic inflammatory response syndrome and sepsis in the critically ill patient? Intensive Care Med. 2002;28:1351-56.
Gleeson, et al. The effect of severe eccentric exercise-induced muscle damage on plasma elastase, glutamine and zinc concentrations. Eur. J. Appi. Physiol. 1998;77:543-546.
Gogos, et al. PR- versus Anti-inflammatory Cytokine Profile in Patients with Severe Sepsis: A Marker for Prognosis and Future Therapeutic Options. J. Infect. Dis 2000;181:176-80.
Gohji, et al. Elevation of Serum Levels of Matrix Metalloproteinase-2 and -3 as New Predictors of Recurrence in Patients with Urothelial Carcinoma. Cancer 1996;78:2379-2387.
Goto, et al. Enhanced Shear-Induced Platelet Aggregation in Acute Myocardial Infarction. Circulation 1999;99:608-613.
Gruber, et al. Markedly Elevated Serum MMP-9 (Gelatinase B) Levels in Rheumatoid Arthritis: A Potentially Useful Laboratory Marker. Clin. Immunol Immunopathol. 1996;78:161-171.
Hama, et al. Detection of C-type natriuretic peptide in human circulation and marked increase of plasma CNP level in septic shock patients. Biochem Biophys Res Commun. Feb. 15, 1994;198(3):1177-82.
Hammerman, et al. Endothelia cell nitric oxide production in acute chest syndrome. Am. J. Physiol. 1999;277:H1579-H1592.
Hanley, et al. The Meaning and Use of the Area under a Receiver Operating Characteristic (ROC) Curve. Radiology 1982;143: 29-36.
Harbarth, et al. Diagnostic Value of Procalcitonin, Interleukin-6, and lnterleukin-8 in Critically Ill Patients Admitted with Suspected Sepsis. Am. J. Respir. Crit. Care Med. 2001;164:396-402.
Hasegawa, et al. Increased levels of Calbindin-D in Serum and Urine from Patients Treated by Extracorporeal Shock Wave Lithotripsy. J. Urol. 1993;149:1414-1418.
Hausfater, et al. Usefulness of procalcitonin as a marker of systemic infection in emergency department patients: a prospective study. Clin Infect Dis. Apr. 1, 2002;34(7):895-901.
Hayasaka, et al. elevated Plasma Levels of Matrix Metalloproteinase-9 (92-kd type IV collagenase/gelatinase B) in Hepatocellular Carcinoma. Hepatology 1996;24:1058-1062.
Haznedaroglu, et al. Selections and IL-6 during the Clinical Course of idiopathic Thrombocytopenic Purpura. Acta Haematol. 1999;101:16-20.
Hirashima, et al. Cerebrospinal fluid tissue factor and thrombin-antithrombin III complex as indicators of tissue injury after subarachnoid hemorrhage. Stroke 1997;28:1666-1670.
Hoffmeister, et al. Correlation between coronary morphology and molecular markers of fibrinolysis in unstable angina pectoris. Atherosclerosis 1999;144:151-157.
Hollander, et al. Risk Stratification of Emergency Department Patients with Acute Coronary Syndromes Using P-Selectin. J. Am. Coll. Cardiol. 1999;34:95-105.
Holvoet, et al. Malondialdehyde-Modified LDL as a Marker of Acute Coronary Syndromes. JAMA 1999;281:1718-1721.
Holvoet, et al. Oxidized LDL and Malondialdehyde-Modified LDL in Patients with Acute Coronary Syndromes and Stable Coronary Artery Disease. Circulation 1998;98:1487-1494.
Holvoet, Oxidative modification of low-density lipoproteins in atherothrombosis Acta Cardiol. 1998;53:253-260.
Hunt, et al. The Amino-Terminal Portion of Pro-brain Natriuretic Peptide (Pro-BNP) Circulates in Human Plasma. Biochem. Biophys. Res. Commun. 1995;214: 1175-83.
Huse, et al. Application of a Filamentous Phage pV1II Fusion Protein System Suitable for Efficient Production, Screening and Mutagenesis of F(ab) Antibody Fragments. J. Immunol. 1992;149,3914-3920.
Hwang, et al. Circulating Adhesion Molecules VCAM-1, ICAM-1, and E-selectin in Carotid Atherosclerosis and Incident Coronary heart Disease Cases. Circulation 1997;96:4219-4225.
iHOP (Information Hyperlinked Over Proteins), entry for CRP, downloaded from ihop-net.org/UniPub/iHOP/gs/92774.html on Jan. 16, 2007.
iHOP (Information Hyperlinked Over Proteins), entry for TNFRSF1A, p. 1, downloaded from ihop-net.org/UniPub/iHOP/gs/92774.html on Jan. 17, 2007.
Iiyama, et al. Patterns of Vascular Cell Adhesion Molecule-1 and Intercellular Adhesion Molecule-1 Expression in Rabbit and Mouse Atherosclerotic Lesions and at Sites Predisposed to Lesion Formation. Circ. Res. 1999;85:199-207.
Ikeda, et al. Increased Soluble Form of P-Selectin in Patients with Unstable Angina. Circulation 1995;92:1693-1696.
Ikeda, et al. Soluble form of P-selectin in Patients with acute myocardial infarction. Coron. Artery Dis. 1994;5:515-518.
International search report Aug. 17, 2006 from PCT Application No. US04/031769.
International search report Jan. 29, 2009 for PCT Application No. US2008/068667.
International search report Feb. 13, 2008 from PCT Application No. US 2006/038755.
Jacque, et al. Myelin Basic Protein in CSF and Blood. Arch. Neurol. 1982;9:557-560.
Jaimes, et al. The systemic inflammatory response syndrome (SIRS) to identity infected patients in the emergency room. Int. Care Med published electronically Jun. 26, 2003;29:1368-71.
James, The variable morphological coexistence of apoptosis and necrosis in human myocardial infarction: significance for understanding its pathogenesis, clinical course, diagnosis and prognosis. Coron. Artery Dis. 1998;9:291-307.
Janoff, Elastase in Tissue Injury. Annu Rev Med 1985;36:207-216.
Jensen, et al. Characterization of Human Brain S100 Protein Fraction: Amino Acid Sequence of Sloop. J. Neurochem. 1985;45:700-705.
Jiminez, et al. Nitric Oxide Production and Inducible Nitric Oxide Synthase Expression in Peritoneal Macrophages of Cirrhotic Patients. Hepatology 1999;30:670-676.
Johnson, et al. Activation of Matrix-Degrading Metalloproteinases by Mast Cell Proteases in Atherosclerotic Plaques. Arterioscler. Thromb. Vasc. Biol. 1998;18:1707-1715.
Johnsson, Markers of Cerebral Ischemia After Cardiac Surgery. Cardiothorac. Vasc. Anesth 1996;10:120-126.
Johnston, et al. Structure of the Human Gene encoding Granule Membrane Protein-140, a Member of the Selection Family of Adhesion Receptors for Leukocytes. J. Biol. Chem, 1990;265:21381-21385.
Jones et al. Elevated brain natriuretic peptide in septic patients without heat failure. Annals of emergency Medicine, 2003;42(5):71 4-715.
Kai, et al. Peripheral Blood levels of Matrix Metalloproteases-2 and -9 Are Elevated in Patients with Acute Coronary Syndromes. J. Am. Coll. Cardiol. 1998;32:368-372.
Kaikita, et al. Soluble P-Selectin is Released into the Coronary Circulation after Coronary Spasm. Circulation 1995;92:1726-1730.
Kaikita, et al. Tissue Factor Expression on Macrophages in Coronary Plaques in Patients with Unstable Angina. Arterioscier. Thromb. Vasc. Biol. 1997;7:2232-2237.
Kaneko, et al. Measurement of plasma annexin V by ELISA in the early detection of acute myocardial infarction. J. Rheumatol. 1999;26:568-573.

Katayama, et al. Soluble P-selectin is present in normal circulation and its plasma level is elevated in patients with thrombotic thrombocytopenic purpura and haemolytic uraemic syndrome. Br. J. Haematol 1993;84:702-710.

Kaye, et al. The Failing Human Heart does not Release Nitrogen Oxides. Life Sci 1998;62:883-887.

Kerbaul, et al. High concentrations of N-BNP are related to non-infectious severe Sirs associated with cardiovascular dysfunction occurring after off-pump coronary artery surgery. Br J Anaesth. Nov. 2004;93(5):639-44.

Keyszer, et al. Circulating Levels of Matrix Metalloproteinases MMP-3 and MMP-1, Tissue Inhibitor of Metalloproteinases 1 (TIMP-1), and MMP-1/TIMP-1 Complex in Rheumatic Disease. Correlation with Clinical Activity of Rheumatoid Arthritis versus Other Surrogate Markers. J. Rheumatol. 1999;26:251-258.

Keyszer, et al. Matrix Metalloproteinases, but not cathepsins B, H, and L or their inhibitors in peripheral blood of patients with rheumatoid arthritis are potentially useful markers of disease activity. Z Rheumatol. 1998;57:392-398.

Kienast, et al. Prothrombin Activation Fragment 1+2 and Thrombin Antithrombin III Complexes in Patients with Angina Pectoris: Relation to the Presence and Severity of Coronary Atherosclerosis. Thromb. Haemost. 1993;70:550-553.

Kim, Cytokines and adhesion molecules in stroke and related diseases. J. Neurol. Sci. 1996;137:69-78.

Kim, et al. Kidney as a Major Clearance Organ for Recombinant Human Interleukin-1 Receptor Antagonist. J. Pharm. Sci. 1995;84:575-580.

Kim, et al. Structure of the Mouse IL-10 Gene and Chromosomal Localization of the Mouse and Human Genes. J. Immunol. 1992;148:3618-23.

Kimura, et al. Plasma concentration of cytokine antagonists in patients with infection following liver resection. British Journal of Surgery. Dec. 1998; 85:1631-1635.

Kiso, et al. Solution-Phase Synthesis of Porcine Brain Natriuretic Peptide (pBNP) Using S-Trimethylacetamido-methylcysteine. Chem. Pharm. Bull. (Tokyo) 1990;38:1192-99.

Knapp, et al. Cutting edge: expression patterns of surface and soluble triggering receptor expressed on myeloid cells-1 in human endotoxemia. J Immunol. Dec. 15, 2004;173(12):7131-4.

Knaus, et al. The APACHE III prognostic system. Risk prediction of hospital mortality for critically ill hospitalized adults. Chest. Dec. 1991;100(6):1619-36.

Kobayashi, et al. Kl-6: A Serum Marker for Interstitial Pneumonia. Chest 1995;108: 311-15.

Kohno, Serum marker KL-6/MUC1 for the diagnosis and management of interstitial pneumonitis. J. Med. Invest. 1999;46:151-58.

Kollef, et al. A rapid assay for the detection of circulating D-dimer is associated with clinical outcomes among critically ill patients. Critical Care Medicine. Jun. 1998;26(6):1054-1060.

Koller, et al. Clinical value of monitoring eosinophil activity in asthma. Arch. Dis. Childhood 1995;73:413-7.

Kosar, et al. Plasma Leukocyte Elastase Concentration and Coronary Artery Disease. Angiology 1998;49:193-201.

Koyama, et al. Determination of plasma tissue factor antigen and its clinical significance. Br. J. Haematol. 1994;87:343-347.

Krupinski, et al. Protein kinase C expression and activity in the human brain after ischaemic stroke. Acta Neurobiol. Exp. (Warz) 1998;58:13-21.

Kurimoto, et al. Plasma platelet-derived growth factor-B chain is elevated in patients with extensively large brain tumour. Acta Neurochir. (Wien) 1995;137:182-187.

Kuwasako, et al. Increased plasma proadrenomedullin N-terminal 20 peptide in patients with essential hypertension. Ann. Clin. Biochem. 1999;36:622-8.

Landi, et al. Hypercoagulability in acute stroke: Prognostic Significance. Neurology 1987;37:1667-1671.

Laskowitz, et al. Serum Markers of Cerebral Ischemia. J. Stroke Cerebrovasc. Dis. 1998;7:234-241.

Latini, et al. Cytokines in Acute Myocardial Infarction: Selective Increase in Circulation Tumor Necrosis Factor, Its Soluble Receptor, and lnterleukin-1 Receptor Antagonist. J. Cardiovasc. Pharmacol. 1994;23:1-6.

Laurino, et al. Thrombus Precursor Protein and the Measurement of Thrombosis in Patients with Acute Chest Pain Syndrome. Ann. Clin. Lab. Sci. 1997;27:338-345.

Lee, et al. Insulin-like Growth Factors and Cerebral schemia. Ann. N. Y. Acad. Sci. 1993;679:418-422.

Lee, et al. Proteolytic Processing of Big Endothelin-3 by the Kell Blood Group Protein. Blood 1999;94:1440-50.

Lein, et al. Metalloproteinasen (MMP-1, MMP-3) and ihre Inhibitoren (TIMP) im Blutplasma bei Patienten mit Prostatakarzinom. Urologe A 1998;37:377-381.

Lein, et al. Metalloproteinases (MMP-1, MMP-3) and their inhibitors (TIMP) in blood plasma of patients with prostate carcinoma. Urologe A. 1998;37(4): 377-381 (English abstract only).

Li, et al. Acute Ischemic Heart Disease, Am. Heart J. 1999;137:1145-1152.

Li, et al. The expression of monocyte chemotactic protein (MCP-1) in human vascular endothelium in vitro and in vivo. Mol. Cell. Biochem. 1993;126:61-68.

Ling, et al. Oxidized or Acetylated Low Density Lipoproteins are Rapidly Cleared by the Liver in Mice with Disruption of the Scavenger Receptor Class A Type I/II Gene. J. Clin. Invest. 1997;100:244-252.

Liras, et al. Clinical value of an automated granulocyte elastase assay in predicting severity of acute pancreatitis. Rev Esp Enferm Dig. Sep. 1985;87(9):641-52. (In Spanish with English abstract).

Liras, et al. Utilidad pronostica de un ensayo automatizado de elastasa granulocitica en pancreatitis aguda. Rev. Esp. Enferm. Dig. 1995;87:641-652.

Livrea, et al. Oxidative Modification of Low-density Lipoprotein and Atherogenic Risk in β-Thalssemia. Blood 1998;98:3936-3942.

Iizasa, et al. Elevated Levels of Circulating Plasma Matrix Metalloproteinase 9 in Non-Small Cell Lung Cancer Patients. Clin. Cancer Res. 1999;5:149-153.

Long, et al. p53 and the Hypoxia-induced Apoptosis of Cultured Neonatal Rat Cardiac Myocytes. J. Clin. Invest. 1997;99:2635-2643.

Isgro, et al. A predictive parameter in patients with brain related complications after cardiac surgery? Eur. J. Cardiothorac. Surg. 1997; 11:640-644.

Lundblad, et al. Endothelin concentrations in experimental sepsis: profiles of big endothelin and endothelin 1-21 in lethal peritonitis in rats. Eur J Surg. Jan. 1995;161(1):9-16.

MacManus, et al. Cerebral lschemia Produces Laddered DNA Fragments Distinct from Cardiac Ischemia and Archetypal Apoptosis. J. Cereb. Blood Flow Metab. 1999;19:502-510.

Maeder, et al. Elevation of B-type natriuretic peptide levels in acute respiratory distress syndrome. Swiss Medical Weekly 2003;13:515-518.

Mahadevan, et al. Structural Role of Extracellular Domain 1 of α-Platelet-derived Growth Factor (PDGF) Receptor for PDGF-AA and PDGF-BB Binding. J. Biol. Chem. 1995;270:27595-27600.

Maisel, A. Algorithms for using B-type natriuretic Peptide levels in the diagnosis and management of congestive heart failure. Crit Path. Cardiol. Jun. 2002;1(2):67-73.

Maisel, A. Practical approaches to treating patients with acute decompensated heart failure. J Card Fail. Jun. 2001;7(2 Suppl 1):13-7.

Maisel, et al. Measuring BNP Levels in the Diagnosis and Treatment of CHF. The Journal of Critical Illness. 2002;17(11): 1-10.

Maiuri, et al. Serum and cerebrospinal fluid enzymes in subarachnoid haemorrhage. Neurol. Res. 1989;11:6-8.

Majetschak, et al. Extracellular ubiquitin inhibits the TNF-α response to endotoxin in peripheral blood mononuclear cells and regulates endotoxin hyporesponsiveness. Blood 2003;101:1882-90.

Manicourt, et al. Serum Levels of Collagenase, Stromelysin-1, and TIMP-1. Arthritis Rheum. 1994;37:1774-1783.

Manten, et al. Procoagulant and proinflammatory activity in acute coronary syndromes. Cardiovasc. Res. 1998;40:389-395.

Marshall et al. Multiple Organ Dysfunction Score: a reliable descriptor of a complex clinical outcome. Critical Care Medicine. Oct. 1995;23(10): 1638-52.

Martens, et al. Serum S-100 and Neuron-Specific Enolase for Prediction of Regaining Consciousness after Global Ischemia. Stroke 1998;29:2363-2366.

Martin, et al. Reactive Hyperemia and Interleukin 6, Interleukin 8, and Tumor Necrosis Factor-α in the Diagnosis of Early-Onset Neonatal Sepsis. Pediatrics 2001;108:1-6.

Matsumori, et al. Plasma Levels of the Monocyte Chemotactic and Activating Factor/ Monocyte Chemoattractant Protein-1 are Elevated in Patients with Acute Myocardial Infarction. J. Mol. Cell. Cardiol. 1997;29:419-423.

Mehta, et al. Neutrophil Function in Ischemic Heart Disease. Circulation 1989;79:549-556.

Meisner, M. Pathobiochemistry and clinical use of procalcitonin. Clin Chim Acta. Sep. 2002;323(1-2):17-29.

Merlini, et al. Persistent Activation of Coagulation Mechanism in Unstable Angina and Myocardial Infarction. Circulation 1994;90:61-68.

Michelson, et al. In vivo tracking of platelets: Circulating degranulated platelets rapidly lose surface P-selectin but continue to circulate and function. Proc. Natl. Acad. Sci. U.S.A. 1996;93:11877-11882.

Migeotte, et al. Identification and characterization of an endogenous chemotactic ligand specific for FPRL2. J Exp Med. Jan. 3, 2005;201(1):83-93.

Missler, et al. S-100 Protein and Neuron-Specific Enolase Concentrations in Blood as Indicators of Infarction Volume and Prognosis in Acute Ischemic Stroke. Stroke 1997;28:1956-1960.

Misumi, et al. Comparison of Plasma Tissue Factor Levels in Unstable Angina Pectoris. Am. J. Cardiol. 1998;8122-26.

Mitaka, et al. Endothelin-1 and atrial natriuretic peptide in septic shock. Am Heart J. Aug. 1993;126(2):466-8.

Mitaka, et al. Increased plasma concentrations of brain natriuretic peptide in patients with acute lung injury. J Crit Care. Jun. 1997;12(2):66-71.

Miwa, et al. Soluble E-selectin, ICAM-1 and VCAM-1 levels in systemic and coronary circulation in patients with variant angina. Cardiovasc. Res. 1997;36:37-44.

Miyata, et al. Conformational Changes in the A! Domain of von Willebrand Factor Modulating the Interaction with Platelet Glycoprotein Ibα. J. Biol. Chem. 1996;271:9046-9053.

Montalescot, et al. Early Increase of von Willebrand Factor Predicts Adverse Outcome in Unstable Coronary Artery Disease. Circulation 1998;98:294-299.

Moore, et al. Collagenase Expression in Ovarian Cancer Cell Lines. Gynecol. Oncol. 1997;65:78-82.

Mooser, et al. Effect of Cardiopulmonary Bypass and Heparin on Plasma Levels of Lp(a) and Apo(a) Fragments. Arterioscler. Thromb. Vasc. Biol. 1999;19:1060-1065.

Mostafavi, et al. Synthesis, Purification and Biological Activity of (SER[10]—Phosphatidyl)-Urodilatin (Phosphourodilatin). Biomed. Pept. Proteins Nucleic Acids 1995;1:255-60.

Mowla, et al. Biosynthesis and Post-translational Processing of the Precursor to Brain-derived Neurotrophic Factor. J. Biol. Chem. 2001;276:12660-6.

Mulvihill, et al. Early Temporal Expression of Soluble Cellular Adhesion Molecules in Patients with Unstable Angina and Subendocardial Myocardial Infarction. Am. J. Cardiol. A9, 1999;83:1265-7.

Mun-Bryce, et al. Matrix Metalloproteinases in Cerebrovascular Disease. J. Cereb. Blood Flow Metab. 1998;18:1163-1172.

Murawaki, et al. Clinical usefulness of serum matrix metalloproteinase-2 in patients with chronic viral liver disease. J. Hepatol. 1999;30:1090-1098.

Murawaki, et al. Serum matrix metalloproteinase-1 in patients with chronic viral hepatitis. J. Gastroenterol. Hepatol. 1999;14:138-145.

Murdoch, et al. The role of chemokines in sepsis and septic shock. Contrib Microbiol. 2003;10:38-57.

Nakamura, et al. Modulation of Plasma Metalloproteinase-9 Concentrations and Peripheral Blood Monocyte mRNA Levels in Patients with Septic Shock: Effect of Fiber-Immobilized Polymyxin B Treatment. Am. J. Med. Sci. 1998; 316:355-360.

Ng, et al. Biomedical applications of protein chips. J. Cell Mol. Med. 2002; 6:329-340.

Ni, et al. Immunochemical Analysis of Some Proteins in Cerebrospinal Fluid and Serum of Patients with Ischemic Strokes. Kidney Int. 1997;52:195-201.

Niebroj-Dobosz, et al. Immunochemical analysis of some proteins in cerebrospinal fluid and serum of patients with ischemic strokes. Folia Neuropathol. 1994;32:129-137.

Nishiyama, et al. Simultaneous Elevation of the Levels of Circulating Monocyte Chemoattractant Protein-1 and Tissue Factor in Acute Coronary Syndromes. Jpn. Circ. J. 1998;62:710-712.

Nishizawa, et al. Protein kinase C6 and α are involved in the development of vasospasm after subarachnoid hemorrhage. Eur. J. Pharmacol. 2000;398:113-119.

Nomura, et al. Effect of Cilostazol on soluble Adhesion Molecules and Platelet-derived Microparticles in Patients with Diabetes. Thromb. Haemost. 1998;80:388-392.

O'Connor, et al. Usefulness of Soluble and Surface-Bound P-Selectin in Detecting Heightened Platelet Activity in Patients with Congestive Heart Failure. Am. J. Cardiol 1999; 83:1345-1349.

Ogawa, et al. Plasma Platelet-Derived Growth Factor Levels in Coronary Circulation and Unstable Angina Pectoris. Am. J. Cardiol. 1992;69:453-456.

Ogawa, et al. Plasma Soluble Intercellular Adhesion Molecule-1 Levels in Coronary Circulation in Patients with Unstable Angina. Am. J. Cardiol. 1999;83:38-42.

Ogawa, et al. Platelet-derived growth factor is released into the coronary circulation after coronary spasm. Coron. Artery Dis. 1993;4:437-442.

Ohtsuka, et al. Clinical implications of circulating soluble Fas and Fas ligand in patients with acute myocardial infarction. Coron. Artery Dis. 1999;10:221-225.

O'Reilly, et al. Endotoxin, sepsis, and the primrose path. Shock. Dec. 1999;12(6):411-20.

Otsuki, et al. Circulating Vascular Cell Adhesion Molecule-1 (VCAM-1) in Atherosclerotic NIDDM Patients. Diabetes 1997;46:2096-2101.

Palfreyman, et al. Radioimmunoassay of Serum Myelin Basic Protein and its Application to Patients with Cerebrovascular Accident. Clin. Chim. Acta 1979;92:403-409.

Pellegatta, et al. Soluble E-Selectin and Intercellular Adhesion Molecule-1 Plasma Levels Increase during Acute Myocardial Infarction. J. Cardiovasc. Pharmacol. 1997;30:455-460.

Persson, et al. S-100 Protein and Neuron-Specific Enolase in Cerebrospinal Fluid and Serum: Markers of Cell Damage in Human Central Nervous System. Stroke 1987;18:911-918.

Peter, et al. Circulating Vascular Cell Adhesion Molecule-1 Correlates with the Extent of Human Atherosclerosis in Contrast to Circulating Intercellular Adhesion Molecule-1, E-Selectin, P-Selectin, and Thrombomodulin. Arterioscler. Thromb. Vasc. Biol. 1997;17:505-512.

Plow, et al. Neutophil Secretion During Blood Coagulation: Evidence for a Prekallikrein Independent Pathway. Thromb. Haemost. 1988;59:360-363.

Plow, Leukocyte Elastase Release during Blood Coagulation. J. Clin. Invest. 1982;69:564-572.

Polin, et al. Detection of soluble E-selectin, ICAM-1, VCAM-1, and L-selectin in the cerebrospinal fluid of patients after subarachnoid hemorrhage. J. Neurosurg. 1998;89:559-567.

Prickett, et al. Identification of Amino-Terminal Pro-C-Type Natriuretic Peptide in Human Plasma. Biochem. Biophys. Res. Commun. 2001;286:513-7.

Quinn, et al. Mapping of Antigenic Sites in Human Neuron-Specific Enolase by Expression Subcloning. Clin. Chem. 1994;40:790-795.

Rangel-Frausto, The Natural History of the Systemic Inflammatory Response Syndrome (SIRS). JAMA 1995;273(2):117-23.

Rau, et al. Serum amyloid A versus C-reactive protein in acute pancreatitis: Clinical value of an alternative acute-phase reactant. Crit Care Med. Mar. 2000;28(3):736-42.

Ray, et al. Predictive Factors of Tumor Response and Prognostic Factors of Survival during Lung Cancer Chemotherapy. Cancer Detect. Prev. 1998;22:293-304.

Rivers, et al. Early goal-directed therapy in the treatment of severe sepsis and septic shock. N. Engl J Med. 2001; 345(19): 1368-77.

Romanic, et al. Matrix Metalloproteinase Expression Increases after Cerebral Focal Ischemia in Rats. Stroke 1998;29:1020-1030.

Rosenberg, Matrix Metalloproteinases in Brain Injury. J. Neurotrauma 1995;12:833-842.

Rossi, et al. Increased Plasma Levels of Platelet-Derived Growth Factor (PDGF-BB+PDGF-AB) in Patients with Never-Treated Mild Essential Hypertension. Am. J. Hypertens. 1998;11:1239-1243.

Rossi, et al. Natriuretic Peptide Levels in Atrial Fibrillation. Journal of the American College of Cardiology 2000;35:1256-62.

Rubatu, et al. The Gene Encoding Atrial Natriuretic Peptide and the Risk of Human Stroke. Circulation 1999;100:1722-6.

Rucinski, et al. Clearance of human platelet factor 4 by liver and kidney: its alteration by heparin. Am. J. Physiol. 1986;251:H800-H807.

Sagnella, Measurement and significance of circulating Natriuretic peptides in cardiovascular disease Clinical Science 1998;95:519-29.

Sakamaki, et al. Soluble Form of P-selectin in Plasma is Elevated in Acute Lung Injury. A. J. Respir. Crit. Care Med. 1995;151:1821-1826.

Sakata, et al. Characteristics of Vasospastic Angina with Increased-Induced Ischemia—Analysis of Parameters of Hemostasis and Fibrinolysis. Jpn. Circ. J. 1996;60:277-284.

Salier, et al. The inter-∞-inhibitor family: from structure to regulation. Biochem. J. 1996;315:1-9.

Sands, et al. Epidemiology of sepsis syndrome in 8 academic medical centers. JAMA. 1997;287(3): 234-240.

Saraste, Morphologic Criteria and Detection of Apoptosis. Herz 1999;24:189-195.

Sasagawa, et al. The Significance of Plasma Lysophospholipids in Patients with Renal Failure on Hemodialysis. J. Nutr. Sci. Vitaminol. (Tokyo) 1998;44:809-818.

Sawicki, et al. Localization and Translocation of MMP-2 during Aggregation of Human Platelets. Thromb. Haemost. 1998;80:836-839.

Schabiltz, et al. Intraventricular Brain-Derived Neurotrophic Factor Reduces Infarct Size after Focal Cerebral Ischemia in Rats. J. Cereb. Blood Flow Metab. 1997;14:500-506.

Schaller, et al. Elevated levels of head activator in human brain tumors and in serum of patients with brain and other neurally derived tumors. J Neurooncol. 1988;6:251-258.

Schins, et al. Epidemiological evaluation of release of Monocyte TNF-α as an exposure and effect marker in pneumonoconiosis: a five year follow up study of coal miners. Occup. Environ. Med. 1995;52:441-50.

Schwab, et al. Plasma Insulin-like Growth Factor I and IGF Binding Protein 3 Levels in Patients with Acute Cerebral Ischemic Injury. Stroke 1997;28:1744-1748.

Schwartz, et al. Tryptase Levels as an Indicator of Mast-Cell Activation in Systemic Anaphylaxis and Mastocytosis, N. Engl. J. Med. 1987;316:1622-26.

Scott, et al. Searching for Peptide Ligands with an Epitope Library. Science 1990;249:386-88.

Seki, et al. Sustained Activation of Blood Coagulation in Patients with Cerebral Thrombosis. Blood Coagul. Fibrinolysis 1997;8:391-396.

Seymour, et al. Tissue platelet derived-growth factor (PDGF) predicts for shortened survival and treatment failure in advanced breast cancer. Breast Cancer Res. Treat. 1993 ;26:247-252.

Shah, et al. Human Monocyte-Derived Macrophages Induce Collagen Breakdown in Fibrous Caps of Atherosclerotic Plaques. Circulation 1995;92:1565-1569.

Shibata, et al. Effect of Magnesium Sulfate Pretreatment and Significance of Matrix Metalloproteinase-1 and Interleukin-6 Levels in Coronary Reperfusion Therapy for Patients with Acute Myocardial Infarction. Angiology 1999;50:573-582.

Shimomura, et al. Serial Changes in Plasma Levels of Soluble P-selectin in Patients with Acute Myocardial Infarction. Am. J. Cardiol. 1998;81:397-400.

Shyu, et al. Serum levels of intercellular adhesion molecule-1 and E-selectin in patients with acute ischaemic stroke. J. Neurol. 1997;244:90-93.

Siess, Lysophostphatidic acid mediates the rapid activation of platelets and endothelial cells by mildly oxidized low density lipoprotein and accumulates in human atherosclerotic lesions. Proc. Natl. Acad. Sci. U.S.A. 1999;96: 6931-6936.

Silver et al. BNP Consensus Panel 2004: a Clinical Approach for the Diagnostic, Prognostic, Screening, Treatment Monitoring, and Therapeutic Roles of Natriuertic Peptides in Cardiovascular Diseases. CHF. 2004;10(5 suppl3):1-30.

Sixma, et al. Von Willebrand Factor and the Blood. Mayo Clin. Proc. 1991;66:628-633.

Skogseid, et al. Increased Serum Creatine Kinase Bb and Neuron Specific Enolase Following Injury indicated Brain Damage. Acta Neurochir. (Wien.) 1992;115:106-111.

Slotwinski, et al. The soluble tumor necrosis factor receptor I is an early predictor of local infective complications after colorectal surgery. J. Clin Immunol. Sep. 2002; 22(5):289-96.

Sobel, et al. Circulating Platelet Products in Unstable Angina Pectoris. Circulation 1981;63:300-306.

Soejima, H. et al., "Angiotensin-Converting Enzyme Inhibition Reduces Monocyte Chemoattractant Protein-1 and Tissue Factor Levels in Patients with Myocardial Infarction." J. Am. Coll. Cardiol. 34:983-988, (1999).

Soejima, H. et al., "Heightened Tissue Factor Associated with Tissue Factor Pathway inhibitor and Prognosis in Patients with Unstable Angina." Circulation 99:2908-2913, (1999).

Sorbi, et al. Elevated Levels of 92-kd Type IV Collagenase (Matrix Metalloproteinase 9) in Giant Cell Arteritis. Arthritis Rheum. 1996;39:1747-1753.

Sorkness, et al. Evaluation of serum eosinophil cationic protein as a predictive marker for asthma exacerbation in patients with persistent disease. Clin. Exp. Allergy 2002;32:1355-59.

Squadrito, F. et al., Thrombolytic therapy with urokinase reduces increased circulating endothelial adhesion molecules in acute myocardial infarction. Inflamm. Res. 45:14-19, (1996).

Steiner, et al. Increased Levels of Soluble Adhesion Molecules in Type 2 (Non-Insulin dependent) Diabetes mellitus are Independent of Glycaemic Control. Thromb. Haemost. 1994;72:979-984.

Stockman, et al. Secondary Structure and Topology of lnterleukin-1 Receptor Antagonist Protein Determined by Heteronuclear Three-Dimensional NMR Spectroscopy. Biochemistry 1992;31:5237-5245.

Suefuji, H. et al., "Increased plasma tissue factor levels in acute myocardial infarction." Am. Heart J. 134:253-259, (1997).

Suga, et al. Clinical significance of MCP-a levels in BALF and serum in patients with interstitial lung diseases. Eur. Respir. J. 1999;14:376-382.

Switalska, et al. Radioimmunoassay of human platelet thrombospondin: Different patterns of thrombospondin and β-thromboglobulin antigen secretion and clearance from the circulation. J. Lab. Clin. Med. 1985;106:690-700.

Taira, et al. Serum B12 Tryptase Level as a Marker of Allergic Airway Inflammation in Asthma. J. Asthma 2002;39:315-22.

Takahashi et al. Tissue Factor in Plasma of Patients with Disseminated Intravascular Coagulation. Am. J. Hematol. 1994;46:333-337.

Takano, et al. Markers of a hypercoagulable state following acute ischemic stroke. Stroke. Feb. 1992;23(2):194-8.

Takeda, I. et al., "Soluble P-selectin in the Plasma of Patients with Connective Tissue Diseases." Int. Arch. Allergy Immunol. 105:128-134, (1994).

Tateyama, et al. Concentration and Molecular Forms of Human Brain Natriuretic Peptide in Plasma. Blochem. Btophys. Res. Commun. 1992;185:760-7.

Tenaglia, A.N. et al., "Levels of Expression of P-Selectin, E-Selectin, and Intracellular Adhesion Molecule-1 in Coronary Atherectomy Specimens from Patients with Stable and Unstable Angina Pectoris." Am. J. Cardiol. 79:742-747, (1997).

Theroux, P. et al., "Fibrinopeptide A and platelet factor levels in unstable angina pectoris." Circulation 75:156-162, (1987).

Thomas, et al. Serum Myelin Basic Protein, Clinical Responsiveness. And Outcome of Severe Head Injury. Acta Neurochir. Suppl. (Wien) 1979;28:93-95.

Tiao et al., "Sepsis is Associated with Increased mRNA's of the Ubiquitin-Proteasome Proteolytic Pathway in Human Skeletal Muscle." J. Clin. Invest. 99:163-168, (1997).

Tohgi, et al. Coagulation-Fibrinolysis Abnormalities in Acute and Chronic Phases of Cerebral Thrombosis and Embolism. Stroke 1990;21:1663-1667.

Tomoda, et al. Plasma soluble P-selectin in acute myocardial infarction: effects of coronary recanalization therapy. Angiology. Oct. 1998;49(10):807-13.

Toouli et al. Guidelines for the Management of Acute Pancreatitis. Journal of Gastroenterology and Hepatology. 2002;17.S15-S39.

Tousoulis, et al. Von Willebrand factor in patients evolving Q-wave versus non-Q-wave acute myocardial infarction. Int J Cardiol. Oct. 25, 1996;56(3):259-62.

Traber, D.L. Tumor necrosis factor and endothelins: team players in shock? J Lab Clin Med. Dec. 1994;124(6):746-7.

Triebel, S. et al., "A 25 kDa $\alpha_2$ microglobulin-related protein is a component of the 125 kDa form of human gelatinase." FEBS Left. 314:386-388, (1992).

Trindade and Rouleau, "Vasopeptidase Inhibitors: Potential Role in the Treatment of Heart Failure." Heart Fail. Monit. 2:2-7, 2001.

Trotter, et al. Immunoreactive Myelin Proteolipid Protein-like Activity in Cerebrospinal Fluid and Serum of Neurologically Impaired Patients. Ann. Neurol. 1983;14:554-558.

Ushiyama, et al. Structural and functional characterization of monomeric soluble P-selectin and comparison with membrane P-selectin. J Biol Chem. Jul. 15, 1993;268(20):15229-37.

Usui, et al. Neural tissue-related proteins (NSE, $G_0\alpha$, 28-kDa calbindin-D, S100b and CK-BB) in serum and cerebrospinal fluid after cardiac arrest. J. Neurol. Sci. 1994;123:134-139.

van den Dorpel, M.A. et al., "Low-density lipoprotein oxidation is increased in kidney transplant recipients." Transpl. Int. 9 Suppl. 1:S54-S57, (1996).

Venge. Serum measurements of eosinophil cationic protein (ECP) in bronchial asthma.Clinical and experimental allergy. 1993; 23 (suppl. 2): 3-7.

Verweij, et al. Full-length von Willebrand factor (vWF) cDNA encodes a highly repetitive protein considerably larger than the mature vWF subunit. EMBO J. Aug. 1986; 5(8): 1839-1847.

Viera, et al. Isolation and expression of human cytokine synthesis inhibitory factor cDNA clones: Homology to Epstein-Barr virus open reading frame BCRFI. Proc. Natl. Acad Sci. USA 1991;88:1172-76.

Villacorta et al. The Role of B-type Natriuretic Peptide in the Diagnosis of Congestive Heart Failure in Patients Presenting to an Emergency Department with Dyspnea. Arq. Bras. Cardiol. 2002;79(6):569-72.

Virchow, et al. Sputum ECP levels Correlate with Parameters of Airflow Obstruction. Am. Rev. Respir. Dis. 1992;146:604-6.

Wallace, et al. The assessment of platelet derived growth factor concentration in post myocardial infarction and stable angina patients. Ann. Clin. Biochem. 1998;35:236-241.

Ward et al., "Binding activities of a repertoire of single immunoglobulin variable domains secreted from *Escherichia coli*." Nature 341:544-546 (1989).

Wilkins, et al. The natriuretic-peptide family. Lancet 1997;349:1307-10.

Wilson, K.M., et al., "Simplified conjugation chemistry for coupling peptides to F(ab') fragments: autologous red cell agglutination assay for HIV-1 antibodies." J. Immunol. Methods 175:267-273; (1994).

Winnikes, et al. Head Activator as a Potential Serum Marker for Brain Tumor Analysis. Eur. J. Cancer 1992;28:421-424.

Witthaut, et al. Plasma atrial natriuretic peptide and brain natriuretic peptide are increased in septic shock: impact of interleukin-6 and sepsis-associated left ventricular dysfunction. Intensive Care Med. 2003;29:1696-1702.

Witthaut, et al. Science review: Natriuretic peptides in critical illness. Crit Care. 2004; 8(5): 342-349.

Woertgen, et al. Comparison of Serial S-100 and NSE Serum Measurements after Severe Head Injury. Acta Neurochir. (Wen) 1997;139:1161-1164.

Xu, Y. et ah, "Lysophosphatidic Acid as a Potential Biomarkerfor Ovarian and other Gynecologic Cancers." JAMA 280:719-723, (1998).

Yamane et al., "Serum Levels of KL-6 as a useful Marker for Evaluating Pulmonary Fibrosis in Patients with Systemic Sclerosis." J. Rheumatol. 27:930-4 (2000).

Yan, et al. Low levels of protein C are associated with poor outcome in severe sepsis. Chest. Sep. 2001;120(3):915-22.

Yap, et al. Contraction to big endothelin-1, big endothelin-2 and big endothelin-3, and endothelin-converting enzyme inhibition in human isolated bronchi. Br. J. Pharmacol. 2000;129:170-6.

Yarmush, M. et al., "Coupling of antibody-binding fragments to solid-phase supports: site-directed binding of F(ab')$_2$ fragments." J. Biochem. Biophys. Methods 25:85-97 (1992).

Yazdani, et al. Percutaneous Interventions Alter the hemostatic Profile of Patients with Unstable versun Stable Angina. J Am Coll Cardiol 1997;30:1284-1287.

Yoneda, et al. Identification of a novel adenylate kinase system in the brain: Cloning of fourth adenylate kinase. Brain Res Mol Brain Res 1998;62:187-195.

Yoshimura, et al. Human Monocyte Chemoattractant protein-1 (MCP-1). FEBS Left. 1989;244:487-493.

Yoshitomi, et al. Plasma levels of adrenomedullin in patients with acute myocardial infarction. Clin. Sci. (Colch) 1998;94:135-9.

Yukioka, et al. Plasma procalcitonin in sepsis and organ failure. Ann Acad Med Singapore. Sep. 2001;30(5):528-31.

Zoccali Cardiac Natriuretic Peptides are Related to Left Ventricular Mass and Function and Predict Mortality in Dialysis Patients. Journal of the American Society of Nephrology. 2001;12(7):1-13.

Zucker, et al. Increased Serum Stromelysin-1 Levels in Systemic Lupus Erythematosus: Lack of Correlation with Disease Activity. J. Rheumatol. 1999;26:78-80.

Llewelyn, et al. Diagnosis of Infection in Sepsis. Int. Care Med. 2001;27: S10-S32.

* cited by examiner

```
                              SEQUENCE LISTING

<160> NUMBER OF SEQ ID NOS: 8

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Arg Val Thr Lys Asp Ala Glu Thr Glu Phe Met Met Ser Lys Leu Pro
 1               5                  10                  15

Leu Glu Asn Pro Val Leu Leu Asp Met Leu Trp Arg Arg Lys Ile Gly
                20                  25                  30

Pro Gln Met Thr Leu Ser His Ala Ala Gly Phe His Ala Thr Ser Ala
            35                  40                  45

Asp Cys Cys Ile Ser Tyr Thr Pro Arg Ser Ile Pro Cys Ser Leu Leu
    50                  55                  60

Glu Ser Tyr Phe Glu Thr Asn Ser Glu Cys Ser Lys Pro Gly Val Ile
65                  70                  75                  80

Phe Leu Thr Lys Lys Gly Arg Arg Phe Cys Ala Asn Pro Ser Asp Lys
                85                  90                  95

Gln Val Gln Val Cys Met Arg Met Leu Lys Leu Asp Thr Arg Ile Lys
            100                 105                 110

Thr Arg Lys Asn
        115

<210> SEQ ID NO 2
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Val Thr Lys Asp Ala Glu Thr Glu Phe Met Met Ser Lys Leu Pro
 1               5                  10                  15

Leu Glu Asn Pro Val Leu Leu Asp Arg Phe His Ala Thr Ser Ala Asp
                20                  25                  30

Cys Cys Ile Ser Tyr Thr Pro Arg Ser Ile Pro Cys Ser Leu Leu Glu
            35                  40                  45

Ser Tyr Phe Glu Thr Asn Ser Glu Cys Ser Lys Pro Gly Val Ile Phe
    50                  55                  60
```

Leu Thr Lys Lys Gly Arg Arg Phe Cys Ala Asn Pro Ser Asp Lys Gln
65                  70                  75                  80

Val Gln Val Cys Met Arg Met Leu Lys Leu Asp Thr Arg Ile Lys Thr
            85                  90                  95

Arg Lys Asn

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Leu Trp Arg Arg Lys Ile Gly Pro Gln Met Thr Leu Ser His Ala
1               5                   10                  15

Ala Gly

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Lys Val Ser Val Ala Ala Leu Ser Cys Leu Met Leu Val Thr Ala
1               5                   10                  15

Leu Gly Ser Gln Ala
            20

<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
            85                  90                  95

Ser Ser Gly Leu Gly Cys Lys Val Leu Arg Arg His
            100                 105

<210> SEQ ID NO 6
<211> LENGTH: 134
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 6

Met Asp Pro Gln Thr Ala Pro Ser Arg Ala Leu Leu Leu Leu Leu Phe
 1               5                  10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Gln Arg Asn
            35                  40                  45

His Leu Gln Gly Lys Leu Ser Glu Leu Gln Val Glu Gln Thr Ser Leu
        50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
                100                 105                 110

Phe Gly Arg Lys Met Asp Arg Ile Ser Ser Ser Ser Gly Leu Gly Cys
            115                 120                 125

Lys Val Leu Arg Arg His
        130

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Leu Trp Arg Arg Lys Ile Gly Pro Gln Met Thr Leu Ser His Ala
 1               5                  10                  15

Ala Gly Cys

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Phe His Ala Thr Ser Ala Asp Cys
 1               5
```

METHODS AND COMPOSITIONS FOR DIAGNOSIS AND/OR PROGNOSIS IN SYSTEMIC INFLAMMATORY RESPONSE SYNDROMES

CROSS-REFERENCE

This application is a national stage entry of PCT/US2008/68667 filed Jun. 27, 2008 which claims priority to U.S. application Ser. No. 11/770,608, filed Jun. 28, 2007 which is a continuation-in-part of U.S. application Ser. No. 11/690,767, filed Mar. 23, 2007 (now abandoned), each of which is incorporated by reference herein in its entirety, including all tables, figures, and claims. This application is related to U.S. application Ser. No. 11/543,312, filed Oct. 3, 2006 (now abandoned), and U.S. application Ser. No. 11/022,552, filed Dec. 23, 2004 (now abandoned), each of which is incorporated by reference herein in its entirety, including all tables, figures, and claims.

SEQUENCE LISTING

The instant application contains a Sequence Listing which has been submitted in ASCII format via EFS-Web and is hereby incorporated by reference in its entirety. Said ASCII copy, created on Mar. 10, 2011, is named 36671-719.831 Seqlist.txt and is 7 Kilobytes in size.

FIELD OF THE INVENTION

The present invention relates to the identification and use of diagnostic markers related to sepsis. In a various aspects, the invention relates to methods and compositions for use in assigning a treatment pathway to subjects suffering from SIRS, sepsis, severe sepsis, septic shock and/or multiple organ dysfunction syndrome.

BACKGROUND OF THE INVENTION

The following discussion of the background of the invention is merely provided to aid the reader in understanding the invention and is not admitted to describe or constitute prior art to the present invention.

The term "sepsis" has been used to describe a variety of clinical conditions related to systemic manifestations of inflammation accompanied by an infection. Because of clinical similarities to inflammatory responses secondary to non-infectious etiologies, identifying sepsis has been a particularly challenging diagnostic problem. Recently, the American College of Chest Physicians and the American Society of Critical Care Medicine (Bone et al., Chest 101: 1644-53, 1992) published definitions for "Systemic Inflammatory Response Syndrome" (or "SIRS"), which refers generally to a severe systemic response to an infectious or non-infectious insult, and for the related syndromes "sepsis," "severe sepsis," and "septic shock," and extending to multiple organ dysfunction syndrome ("MODS"). These definitions, described below, are intended for each of these phrases for the purposes of the present application. For purposes of this invention, each of these represents a progressively more severe SIRS category; that is, sepsis is more severe than SIRS, severe sepsis is more severe than sepsis, septic shock is more severe than severe sepsis, and MODS is more severe than septic shock.

"SIRS" refers to a condition that exhibits two or more of the following:

a temperature >38° C. or <36° C.;
a heart rate of >90 beats per minute (tachycardia);
a respiratory rate of >20 breaths per minute (tachypnea) or a $P_aCO_2$<4.3 kPa; and
a white blood cell count >12,000 per mm$^3$, <4,000 per mm$^3$, or >10% immature (band) forms.

"Sepsis" refers to SIRS, further accompanied by a clinically evident or microbiologically confirmed infection. This infection may be bacterial, fungal, parasitic, or viral.

"Severe sepsis" refers to sepsis, further accompanied by organ hypoperfusion made evident by at least one sign of organ dysfunction such as hypoxemia, oliguria, metabolic acidosis, or altered cerebral function.

"Septic shock" refers to severe sepsis, further accompanied by hypotension, made evident by a systolic blood pressure <90 mm Hg, or the requirement for pharmaceutical intervention to maintain blood pressure.

MODS (multiple organ dysfunction syndrome) is the presence of altered organ function in a patient who is acutely ill such that homeostasis cannot be maintained without intervention. Primary MODS is the direct result of a well-defined insult in winch organ dysfunction occurs early and can be directly attributable to the insult itself. Secondary MODS develops as a consequence of a host response and is identified within the context of SIRS.

A systemic inflammatory response leading to a diagnosis of SIRS may be related to both infection and to numerous non-infective etiologies, including burns, pancreatitis, trauma, heat stroke, and neoplasia. While conceptually it may be relatively simple to distinguish between sepsis and non-septic SIRS, no diagnostic tools have been described to unambiguously distinguish these related conditions. See, e.g., Llewelyn and Cohen, Int. Care Med. 27: S10-S32, 2001. For example, because more than 90% of sepsis cases involve bacterial infection, the "gold standard" for confirming infection has been microbial growth from blood, urine, pleural fluid, cerebrospinal fluid, peritoneal fluid, synnovial fluid, sputum, or other tissue specimens. Such culture has been reported, however, to fail to confirm 50% or more of patients exhibiting strong clinical evidence of sepsis. See, e.g., Jaimes et al., Int. Care Med 29: 1368-71, published electronically Jun. 26, 2003.

The physiologic responses leading to the systemic manifestations of inflammation in sepsis remain unclear. Activation of immune cells occurs in response to the LPS endotoxin of gram negative bacteria and exotoxins of gram positive bacteria. This activation leads to a cascade of events mediated by proinflammatory cytokines, adhesion molecules, vasoactive mediators, and reactive oxygen species. Various organs, including the liver, lungs, heart, and kidney are affected directly or indirectly by this cascade. Sepsis is also associated with disseminated intravascular coagulation ("DIC"), mediated presumably by cytokine activation of coagulation. Fluid and electrolyte balance are also affected by increases in capillary perfusion and reduced oxygenation of tissues. Unchecked, the uncontrolled inflammatory response created can lead to ischemia, loss of organ function, and death.

Despite the availability of antibiotics and supportive therapy, sepsis represents a significant cause of morbidity and mortality. A recent study estimated that 751,000 cases of severe sepsis occur in the United States annually, with a mortality rate of from 30-50%. Angus et al., Crit. Care Med. 29: 1303-10, 2001. Recently, an organization of medical care groups referred to as the "Surviving Sepsis Campaign" issued guidelines for managing subjects suffering from severe sepsis and septic shock. Dellinger et al., Crit. Care Med. 32: 858-873, 2004. These guidelines draw from, amongst other sources, the "Early Goal Directed Therapy" therapy regimen developed by Rivers and colleagues. See, e.g. *New Engl. J. Med.* 345: 1368-77. 2001.

Several laboratory tests have been investigated or proposed for use, in conjunction with a complete clinical examination of a subject, for the diagnosis and prognosis of sepsis. See, e.g., U.S. Pat. Nos. 5,639,617 and 6,303,321; Patent publications US2005/0196817, WO2005/048823, WO2004/046181, WO2004/043236, US2005/0164238; and Charpentier et al., *Crit. Care Med.* 32: 660-65, 2004; Castillo et al., *Int. J. Infect. Dis.* 8: 271-74, 2004; Chua and Kang-Hoe, *Crit. Care* 8: R248-R250, 2004; Witthaut et al., *Int. Care Med.* 29: 1696-1702, 2003; Jones and Kline, *Ann. Int. Med.* 42: 714-15, 2003; Maeder et al., *Swiss Med. Wkly.* 133: 515-18, 2003; Giamarellos-Bourboulis et al., *Intensive Care Med.* 28: 1351-56, 2002; Harbarth et al., *Am. J. Respir. Crit. Care Med.* 164: 396-402, 2001; Martin et al., *Pediatrics* 108: (4) e61 1-6, 2001; and Bossink et al., *Chest* 113: 1533-41, 1998. The use of CCL23 as a marker in sepsis is disclosed in US 2005/0196817 (where it is called by its alternative name MPIF-1) and in WO07/041,623.

BRIEF SUMMARY OF THE INVENTION

The present invention relates to the identification and use of markers for the detection of sepsis, the differentiation of sepsis from other causes of SIRS, and in the stratification of risk in sepsis patients. The methods and compositions of the present invention can be used to facilitate the treatment of patients and the development of additional diagnostic and/or prognostic indicators and therapies.

In various aspects, the invention relates to materials and procedures for identifying markers that may be used to direct therapy in subjects; to using such markers in treating a patient and/or to monitor the course of a treatment regimen; to using such markers to identify subjects at risk for one or more adverse outcomes related to SIRS; and for screening compounds and pharmaceutical compositions that might provide a benefit in treating or preventing such conditions.

In a first aspect, the invention relates to diagnostic methods for identifying a subject suffering from SIRS, sepsis, severe sepsis, septic shock and/or MODS, for distinguishing amongst these conditions, or for assigning a prognosis to a subject suffering from one or more of these conditions. These methods comprise analyzing a test sample obtained from a subject by performing an immunoassay that detects CCL23 splice variant; and relating the immunoassay result to one or more of the following diagnoses: (i) the presence or absence of SIRS, (ii) the presence or absence of sepsis, (iii) the presence or absence of severe sepsis, and (iv) the presence or absence of septic shock. The terms "CCL23 splice variant" and "CCL23" are defined hereinafter.

In a related aspect, the invention relates to methods for distinguishing among SIRS, sepsis, severe sepsis, septic shock and/or MODS. These methods similarly comprise analyzing a test sample obtained from a subject by performing an immunoassay that detects CCL23 splice variant; and relating the immunoassay result to ruling in or out one or more of the following diagnoses: that the subject has SIRS, but not sepsis, severe sepsis, or septic shock; that the subject has sepsis, but not severe sepsis or septic shock; or that the subject has septic shock.

In a related aspect, the invention relates to methods for determining a prognosis for a subject suffering from SIRS, sepsis, severe sepsis, septic shock and/or MODS. These methods similarly comprise analyzing a test sample obtained from a subject by performing an immunoassay that detects CCL23 splice variant; and relating the immunoassay result to the likelihood of a future outcome, either positive (e.g., that the subject is more likely to live, or is at a decreased risk of progressing to a more severe SIRS category) or negative (e.g., that the subject is at an increased risk of death, that the subject is at an increased risk of progressing to a more severe SIRS category).

And in still another related aspect, the invention relates to a method of monitoring a treatment regimen in a subject being treated for SIRS, sepsis, severe sepsis, septic shock and/or MODS. These methods similarly comprise analyzing a test sample obtained from a subject by performing an immunoassay that detects CCL23 splice variant; and relating the immunoassay result to the success or failure of the treatment received by the subject.

As described herein, preferred assays are "configured to detect" CCL23 splice variant, which means that the assay can generate a detectable signal indicative of the presence or amount of a physiologically relevant concentration of CCL23 splice variant. As described hereinafter, such assays may also detect CCL23.

Assays may be configured to not appreciably detect CCL23, thereby providing an immunoassay result that is sensitive for CCL23 splice variant, relative to CCL23 itself. These are referred to herein as "CCL23 splice variant immunoassays" or "CCL23sv immunoassays." In preferred embodiments, however, the immunoassay that detects CCL23 splice variant also detects CCL23, and optionally detects one or more of, and optionally each of, N-terminal processed forms of CCL23 selected from the group consisting of $CCL23_{19-99}$, $CCL23_{22-99}$, $CCL23_{27-99}$, and $CCL23_{30-99}$. These assays, which detect both CCL23 splice variant and CCL23, are referred to herein as "total CCL23 immunoassays" and the results obtained therefrom are refereed to as "total CCL23 assay results." Total CCL23 immunoassays that do not recognize one or more N-terminal processed forms of CCL23 selected from the group consisting of $CCL23_{19-99}$, $CCL23_{22-99}$, $CCL23_{27-99}$, and $CCL23_{30-99}$ are referred to herein as "full length CCL23 immunoassays." Each of these labels is used here for convenience in referring to the various assays, and is not meant to be fully descriptive of such assays. For example, the phrase "full length CCL23 immunoassay" is not meant to imply that such assays necessarily recognize only $CCL23_{1-99}$.

Collectively, the assays configured to detect CCL23 splice variant, whether a CCL23sv immunoassay or a total CCL23 immunoassay, are referred to herein as "CCL23 assays" and the results obtained therefrom are referred to as CCL23 assay results." For the sake of clarity, assays that detect CCL23 but do not appreciably detect CCL23 splice variant are not "CCL23 assays" as that term is used herein. If referred to, such assays will be referred to as being "CCL23-specific."

The CCL23 immunoassays may be described as being "sensitive" or "insensitive" for CCL23 splice variant, relative to CCL23. "Sensitive" assays, as that term is used herein, are configured to provide a signal that is at least a factor of 5, more preferably a factor of ten, and most preferably a factor of 100 or more, greater for CCL23 splice variant at its physiologically relevant concentration as compared to equimolar amounts of CCL23. In the case of assays that are sensitive for CCL23 splice variant, relative to CCL23, such assays preferably employ one or more antibodies that specifically bind CCL23 splice variant, relative to CCL23. As such, the affinity of one or more antibodies used in the immunoassay is at least 5-fold, preferably 10-fold, more preferably 25-fold, even more preferably 50-fold, and most preferably 100-fold or more, greater for CCL23 splice variant than its affinity for CCL23. Such antibodies are preferably directed to an epitope that is present on CCL23 splice variant, but not on CCL23 itself.

"Insensitive" assays, as that term is used herein, are configured to provide a signal that is within a factor of 2, and most preferably a factor of 0.5 or less, for CCL23 splice variant at its physiologically relevant concentration as compared to equimolar amounts of CCL23. Such assays may preferably be formulated using antibodies that have an affinity for CCL23 splice variant, that is within a factor of 2, and most preferably a factor of 0.5 or less, relative to an affinity for CCL23. Alternatively, individual antibodies that separately bind CCL23 splice variant or CCL23 may be combined, either in a single assay, or in separate assays in which the assay results are combined computationally.

The CCL23 assays of the present invention may be used individually in a univariate fashion, or together with additional markers in a multivariate "panel" approach for diagnosis and/or prognosis. Such panels comprise measuring at least one, preferably at least two, more preferably at least three, still more preferably at least four, yet more preferably at least five, and most preferably at least six or more additional markers. These additional markers that may be used together with CCL23 assays of the present invention are described herein, and are preferably selected from the group consisting of markers related to blood pressure regulation, markers related to coagulation and hemostasis, markers related to apoptosis, and/or markers related to inflammation.

In certain preferred embodiments, the methods comprise one or more CCL23 assays of the present invention; and performing one or more additional immunoassays that detect markers selected from the group consisting of NT-proBNP, proBNP, $BNP_{79-108}$, BNP, $BNP_{3-108}$, CCL23, CRP, D-dimer, IL-1ra, NGAL, peptidoglycan recognition protein, procalcitonin, $procalcitonin_{3-116}$, active protein C, latent protein C, total protein C, and sTNFR1a to provide one or more additional immunoassay results.

In this "panel" approach, the relating step comprises relating the CCL23 assay result(s) obtained, and the one or more additional immunoassay results obtained, (1) to one or more of the following diagnoses: (i) the presence or absence of SIRS, (ii) the presence or absence of sepsis, (iii) the presence or absence of severe sepsis, and (iv) the presence or absence of septic shock; (2) to ruling in or out one or more of the following diagnoses: that the subject has SIRS, but not sepsis, severe sepsis, or septic shock; that the subject has sepsis, but not severe sepsis or septic shock; or that the subject has septic shock; (3) to the likelihood of a future outcome, either positive (e.g., that the subject is more likely to live, or is at a decreased risk of progressing to a more severe SIRS category) or negative (e.g., that the subject is at an increased risk of death, that the subject is at an increased risk of progressing to a more severe SIRS category); and/or (4) the success or failure of the treatment received. While exemplary panels are described herein, one or more markers may be replaced, added, or subtracted from these exemplary panels while still providing clinically useful results.

In certain embodiments, the relating step comprises comparing the concentrations of the individual marker(s) to one or more preselected levels (a "threshold"). Thresholds may be selected that provide an acceptable ability to predict diagnosis, prognostic risk, treatment success, etc. In practice, Receiver Operating Characteristic curves, or "ROC" curves, are typically calculated by plotting the value of a variable versus its relative frequency in two populations (called arbitrarily "disease" and "normal" or "low risk" and "high risk" for example). For any particular marker, a distribution of marker levels for subjects with and without a disease will likely overlap. Under such conditions, a test does not absolutely distinguish "disease" and "normal" with 100% accuracy, and the area of overlap indicates where the test cannot distinguish "disease" and "normal." A threshold is selected, above which (or below which, depending on how a marker changes with the disease or prognosis) the test is considered to be "positive" and below which the test is considered to be "negative." The area under the ROC curve is a measure of the probability that the perceived measurement will allow correct identification of a condition. See, e.g., Hanley et al., *Radiology* 143: 29-36 (1982).

Additionally, thresholds may be established by obtaining an earlier marker result from the same patient, to which later results may be compared. In these embodiments, the individual in effect acts as their own "control group." In markers that increase with disease severity or prognostic risk, an increase over time in the same patient can indicate a worsening of disease or a failure of a treatment regimen, while a decrease over time can indicate remission of disease or success of a treatment regimen.

In certain embodiments, markers and/or marker panels are selected to distinguish "disease" and "normal" or, alternatively "low risk" from "high risk" with at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

In other embodiments, a positive likelihood ratio, negative likelihood ratio, odds ratio, or hazard ratio is used as a measure of a test's ability to predict disease, prognostic risk, or treatment outcome. In the case of a positive likelihood ratio, a value of 1 indicates that a positive result is equally likely among subjects in both the first and second groups; a value greater than 1 indicates that a positive result is more likely in the first group; and a value less than 1 indicates that a positive result is more likely in the second group. In the case of a negative likelihood ratio, a value of 1 indicates that a negative result is equally likely among subjects in both groups; a value greater than 1 indicates that a negative result is more likely in the first group; and a value less than 1 indicates that a negative result is more likely in the second group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the first and second groups; a value greater than 1 indicates that a positive result is more likely in the first group; and a value less than 1 indicates that a positive result is more likely in the second group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk is equal in both the first and second groups; a value greater than 1 indicates that the risk is greater in the first group; and a value less than 1 indicates that the risk is greater in the second group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/−5% of a given measurement.

In some cases, multiple thresholds may be determined. This is the case in so-called "tertile," "quartile," or "quintile" analyses. In these methods, the "disease" and "normal" groups (or "low risk" and "high risk") groups are considered together as a single population, and are divided into 3, 4, or 5 (or more) "bins" having equal numbers of individuals. The boundary between two of these "bins" may be considered "thresholds." A risk (of a particular diagnosis or prognosis for example) can be assigned based on which "bin" a test subject falls into.

In other embodiments, particular thresholds for the marker(s) measured are not relied upon to determine if the marker level(s) obtained from a subject are correlated to a particular diagnosis or prognosis, For example, a temporal change in the marker(s) can be used to rule in or out one or more particular diagnoses and/or prognoses. Alternatively, marker(s) are correlated to a condition, disease, prognosis, etc., by the presence or absence of the marker(s) in a particular assay format. And in the case of panels, the present invention may utilize an evaluation of the entire profile of markers to provide a single result value (e.g., a "panel response" value expressed either as a numeric score or as a percentage risk). In such embodiments, an increase, decrease, or other change (e.g., slope over time) in a certain subset of markers may be sufficient to indicate a particular condition or future outcome in one patient, while an increase, decrease, or other change in a different subset of markers may be sufficient to indicate the same or a different condition or outcome in another patient. Methods for performing such analyses are described hereinafter.

The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create an ROC curve. For example, results of a test on "disease" samples might be ranked according to degree (say 1=low, 2=normal, and 3=high). This ranking can be correlated to results in the "normal" population, and a ROC curve created. These methods are well known in the art. See, e.g., Hanley et al., *Radiology* 143:29-36 (1982).

In certain embodiments, markers and/or marker panels are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/−5% of a given measurement.

In certain embodiments, a CCL23sv assay result, total CCL23 assay result, or both, is related to a diagnosis, and the relating step comprises comparing the assay result(s) to predetermined threshold(s) selected to provide a ROC area of at least 0.7 for the diagnosis of sepsis. In alternative embodiments, the CCL23sv immunoassay result is related to a diagnosis of severe sepsis, and the relating step comprises comparing the CCL23sv immunoassay result to a predetermined level of CCL23sv selected to provide a ROC area of at least 0.7 for the diagnosis of severe sepsis. In other embodiments, the CCL23sv immunoassay result is related to a diagnosis of septic shock, and the relating step comprises comparing the CCL23sv immunoassay result to a predetermined level of CCL23sv selected to provide a ROC area of at least 0.7 for the diagnosis of septic shock. In still other embodiments, the CCL23sv immunoassay result is related to a diagnosis of advanced sepsis, and the relating step comprises comparing the CCL23sv immunoassay result to a predetermined level of CCL23sv selected to provide a ROC area of at least 0.7 for the diagnosis of advanced sepsis.

In certain other embodiments, a CCL23sv assay result, total CCL23 assay result, or both, is related a prognosis of near-term mortality, and the relating step comprises comparing the assay result(s) to predetermined threshold(s) selected to provide an odds ratio of at least 2 for the prognostic risk of mortality. Such near-term mortality is death within 7 days, more preferably within 5 days, still more preferably within 3 days, and most preferably within 48 hours. Subjects for whom a prognostic risk is assigned may suffer from SIRS, sepsis, severe sepsis, septic shock or MODS. In certain preferred embodiments, the subject for whom a prognostic risk is assigned suffers from "advanced sepsis."

In certain other embodiments, a CCL23sv assay result, total CCL23 assay result, or both, is related a prognosis of progressing to a worsening sepsis category, and the relating step comprises comparing the assay results) to predetermined threshold(s) selected to provide an odds ratio of at least 2 for the prognostic risk of progressing to a worsening sepsis category. Such risk is assigned for progressing to a worsening sepsis category within 7 days, more preferably within 5 days, still more preferably within 3 days, and most preferably within 48 hours. Subjects for whom a prognostic risk is assigned may suffer from SIRS, sepsis, severe sepsis, septic shock or MODS. In certain preferred embodiments, the subject for whom a prognostic risk is assigned suffers from "advanced sepsis."

In another aspect, the invention relates to a method of formulating a total CCL23 assay, wherein the total CCL23 assay is insensitive for CCL23 splice variant, relative to CCL23.

In certain embodiments, these methods comprise providing at least two antibody populations that bind to an epitope that is present in both CCL23 splice variant and CCL23, and that pair with one another in a sandwich immunoassay format for detection of CCL23 splice variant and CCL23. Such assays may preferably be formulated using antibodies that have an affinity for CCL23 splice variant that is within a factor of 2, and most preferably a factor of 0.5 or less, relative to an affinity for CCL23. In preferred embodiments, one of these antibody populations is detectably labeled, and the other antibody population is attached to a solid phase.

In related embodiments, total CCL23 assays may be formulated by providing separate antibody populations, one of which binds to CCL23 splice variant, and the other of which binds CCL23. These separate antibody populations may be pooled to provide a pooled antibody that acts as if it a single antibody population that binds both CCL23 splice variant and CCL23. That pooled antibody can be used in a sandwich immunoassay format, either with an antibody population that binds to an epitope that is present in both CCL23 splice variant and CCL23 and that pairs with the pooled antibody in a sandwich immunoassay format for detection of CCL23 splice variant and CCL2, or with a second pooled antibody population formed in a similar manner. Again, in preferred embodiments, one of these antibody populations is detectably labeled, and the other antibody population is attached to a solid phase.

Alternatively, separate antibody populations, one of which binds to CCL23 splice variant, and the other of which binds CCL23, may be used in separate assays, one of which is a CCL23sv immunoassay, and the other of which is a CCL23-specific assay. The results are then combined computationally (e.g., by summing the concentrations of CCL23 splice variant and CCL23 obtained from these separate assays) to provide a total CCL23 assay result. Such assays are preferably sandwich assays in which one antibody is detectably labeled, and the other antibody is attached to a solid phase.

In a related aspect, the invention relates to devices to perform one or more of the methods described herein, and methods of their use. Such devices preferably contain a plurality of diagnostic zones, each of which is related to a particular marker of interest. Such diagnostic zones are preferably discrete locations within a single assay device. Such devices may be referred to as "arrays" or "microarrays." Following reaction of a sample with the devices, a signal is generated from the diagnostic zone(s), which may then be correlated to the presence or amount of the markers of interest. Numerous suitable devices are known to those of skill in the art.

Such assay devices are preferably configured to provide reagents for performing the total CCL23 assays described above. In these embodiments, one or more assay zones comprise one or more solid phase antibodies as described in the preceding paragraphs, and the assay device further comprises one or more detectably labeled antibodies as described in the preceding paragraphs. Upon addition of a sample to the device, one or more sandwich assays are performed, from which a total CCL23 assay result is obtained. As noted above, such devices may perform a single assay from which the total CCL23 assay result is obtained, or the total result may be obtained from separate assays, one of which is a CCL23sv immunoassay, and the other of which is a CCL23-specific assay, the results of which are then combined computationally. Most preferably, the total CCL23 assay performed by the device is insensitive for CCL23 splice variant, relative to CCL23.

DETAILED DESCRIPTION OF THE INVENTION

The present invention relates to methods and compositions for symptom-based differential diagnosis, prognosis, and determination of treatment regimens in subjects. In particular, the invention relates to methods and compositions selected to rule in or out SIRS, or for differentiating sepsis, severe sepsis, septic shock, and/or MODS from each other and/or from non-infectious SIRS.

Patients presenting for medical treatment often exhibit one or a few primary observable changes in bodily characteristics or functions that are indicative of disease. Often, these "symptoms" are nonspecific, in that a number of potential diseases can present the same observable symptom or symptoms. In the case of SIRS, the condition exists, by definition, whenever two or more of the following symptoms are present:
- a temperature >38° C. or <36° C.;
- a heart rate of >90 beats per minute (tachycardia);
- a respiratory rate of >20 breaths per minute (tachypnea) or a $P_aCO_2$<4.3 kPa; and
- a white blood cell count >12,000 per $mm^3$, <4,000 per $mm^3$, or >10% immature (band) forms.

The present invention describes methods and compositions that can assist in the differential diagnosis of one or more nonspecific symptoms by providing diagnostic markers that are designed to rule in or out one, and preferably a plurality, of possible etiologies for the observed symptoms. Symptom-based differential diagnosis described herein can be achieved using panels of diagnostic markers designed to distinguish between possible diseases that underlie a nonspecific symptom observed in a patient.

DEFINITIONS

The term "CCL23 splice variant" as used herein refers to a mature polypeptide formed by removal of the signal sequence from the polypeptide described in Swiss-Prot accession number P55773-2. CCL23 splice variant has the following sequence:

```
                                              (SEQ ID NO: 1)
        10         20         30         40         50         60
RVTKDAETEF MMSKLPLENP VLLDMLWRRK IGPQMTLSHA AGFHATSADC CISYTPRSIP 70         80         90        100        110        116
CSLLESYFET NSECSKPGVI FLTKKGRRFC ANPSDKQVQV CMRMLKLDTR IKTRKN.
```

The term "CCL23" as used herein refers to a mature polypeptide formed by removal of the signal sequence from the polypeptide described in Swiss-Prot accession number P55773-1. CCL23 has the following sequence:

```
                                              (SEQ ID NO: 2)
        10         20         30         40         50         60
RVTKDAETEF MMSKLPLENP VLLDRFHATS ADCCISYTPR SIPCSLLESY FETNSECSKP 70         80         90         99
GVIFLTKKGR RFCANPSDKQ VQVCMRMLKL DTRIKTRKN.
```

As is apparent from these sequences, CCL23 splice variant is a longer variant of CCL23, in which $R_{46}$ is replaced by MLWRRKIGPQMTLSHAAG (SEQ ID NO:3). In the case of both CCL23 splice variant and CCL23, the putative secretory signal sequence is represented by residues 1-21 (MKVSVAALSCLMLVTALGSQA, SEQ ID NO: 4), which are presumably lacking from the mature secreted form of each protein.

It has been reported that CCL23—the short form—is the major species and the longer CCL23 splice variant form was detected only in very low abundance. The present invention demonstrates that, in conditions related to SIRS, substantial concentrations of the CCL23 splice variant form can be detected and related to both diagnosis and prognosis, and measurement of this form, or of total CCL23 (meaning both CCL23 and CCL23 splice variant) can provide improved results, relative to measuring CCL23 itself.

Preferred assays are "configured to detect" a particular marker, in this case preferably CCL23 splice variant. Because an antibody epitope is on the order of 8 amino acids, an immunoassay will detect other polypeptides (e.g., related markers) so long as the other polypeptides contain the epitope(s) necessary to bind to the antibody used in the assay. Such other polypeptides are referred to as being "immunologically detectable" in the assay, and would include various isoforms. That an assay is "configured to detect" a marker means that an assay can generate a detectable signal indicative of the presence or amount of a physiologically relevant concentration of a particular marker of interest.

Such an assay may, but need not, specifically detect a particular marker (i.e., detect a marker but not some or all related markers). Thus, an assay that is configured to detect CCL23 splice variant could also detect CCL23 if the antibody used in such an assay recognize an epitope common to both forms. Alternatively, an antibody that recognizes an epitope that is present in CCL23 splice variant but not CCL23 could be used to provide a CCL23sv immunoassay, and an antibody that binds to an epitope that is present in CCL23 but not CCL23 splice variant (such as an epitope formed by the junction around residue $R_{46}$ in CCL23) could be used to provide a CCL23-specific immunoassay.

Additionally, N-terminal processed forms of CCL23, including $CCL23_{19-99}$, $CCL23_{22-99}$, $CCL23_{27-99}$, and $CCL23_{30-99}$, have been reported to be found in high levels in synovial fluids from rheumatoid patients. Because these N-terminal cleavages lie before the insertion at $R_{46}$, an assay that is configured to detect CCL23 splice variant could also detect corresponding N-terminal processed forms of the splice variant.

Immunoassays may be configured in a variety of formats known in the art. In the case of a competitive immunoassay, markers to be detected must contain the epitope bound by the single antibody used in the assay in order to be detected. In the case of a sandwich immunoassay, markers to be detected must contain at least two epitopes bound by the antibody used in the assay in order to be detected. Taking CCL23 splice variant as an example, an assay configured to detect this marker may be configured to be a "total" CCL23 assay by selecting antibodies that bind in the regions that are common to both CCL23 and CCL23 splice variant. Alternatively, an assay may be configured to be specific to CCL23 splice variant, relative to CCL23, by selecting at least one antibody that binds to the splice variant but not to CCL23. It should be recognized that, in a sandwich assay that is specific to CCL23 splice variant relative to CCL23, only one antibody of the antibody pair used needs to be specific for the splice variant, as a signal is only obtained when both antibodies bind to the target polypeptide.

Preferred CCL23 splice variant assays may be described herein as being "sensitive" or "insensitive" for CCL23 splice variant, relative to CCL23. An "insensitive" assay as that term is used with regard to a target molecule is configured to provide a signal that is within a factor of 5, more preferably within a factor of two, and most preferably within 20%, when comparing assay results for equimolar amounts of the target and non-target. A "sensitive" assay as that term is used with regard to a target molecule is configured to provide a signal that is at least a factor of 5, more preferably a factor of ten, and most preferably a factor of 100 or more, greater when comparing assay results for equimolar amounts of the target and non-target. Certain CCL23 splice variant assays are sensitive, relative to CCL23. Particularly preferred CCL23 splice variant assays are insensitive relative to CCL23, and may also optionally bind one or more N-terminal processed forms of CCL23 selected from the group consisting of $CCL23_{19-99}$, $CCL23_{22-99}$, $CCL23_{27-99}$, and $CCL23_{30-99}$.

The term "antibody" as used herein refers to a peptide or polypeptide, or a population of peptides or polypeptides, derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) *Nature* 341:544-546), which consists of a VII domain; and (vi) an isolated complementarity determining region (CDR). Single chain antibodies are also included by reference in the term "antibody."

Preferably the affinity of the antibody in a "sensitive" assay will be at least about 5-fold, preferably 10-fold, more preferably 25-fold, even more preferably 50-fold, and most preferably 100-fold or more, greater for a target molecule than its affinity for a non-target molecule.

The term "specifically binds" is not intended to indicate that an antibody binds exclusively to its intended target. Rather, an antibody "specifically binds" if its affinity for its intended target is about 5-fold greater when compared to its affinity for a non-target molecule. In preferred embodiments, Specific binding between an antibody or other binding agent and an antigen means a binding affinity of at least $10^6$ M$^{-1}$. Preferred antibodies bind with affinities of at least about $10^7$ M$^{-1}$, and preferably between about $10^8$ M$^{-1}$ to about $10^9$ M, about 10 M to about $10^{10}$ M$^{-1}$ or about $10^{10}$ M$^{-1}$ to about $10^{11}$ M$^{-1}$.

Affinity is calculated as $K_d = k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: r/c=K(n−r):

where
r=moles of bound ligand/mole of receptor at equilibrium;
c=free ligand concentration at equilibrium;
K=equilibrium association constant; and
n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat. No. 6,316,409). The affinity of a targeting agent for its target molecule is preferably at least about $1 \times 10^{-6}$ moles/liter, is more preferably at least about $1 \times \times 10^{-7}$ moles/liter, is even more preferably at least about $1 \times 10^{-8}$ moles/liter, is yet even more preferably at least about $1 \times 10^{-9}$ moles/liter, and is most preferably at least about $1 \times 10^{-10}$ moles/liter. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

Certain immunoassays of the present invention utilize at least one antibody that specifically binds CCL23 splice variant (the "target"), relative to CCL23 (the "non-target"), while certain other immunoassays of the present invention utilize antibody that binds both CCL23 and CCL23 splice variant with affinities that are within a factor of 5, and most preferably within a factor of 2 or less.

The term "marker" as used herein refers to proteins, polypeptides, glycoproteins, proteoglycans, lipids, lipoproteins, glycolipids, phospholipids, nucleic acids, carbohydrates, etc. or small molecules to be used as targets for screening test samples obtained from subjects. "Proteins or polypeptides" used as markers in the present invention are contemplated to include any fragments thereof, in particular, immunologically detectable fragments. Markers may post-translationally modified, for example by oxidation of methionine residues, ubiquitination, cysteinylation, nitrosylation (e.g., containing nitrotyrosine residues), halogenation (e.g., containing chlorotyrosine and/or bromotyrosine residues), glycosylation, complex formation, differential splicing, etc. Markers can also include clinical "scores" such as a pre-test probability assignment, a pulmonary hypertension "Daniel" score, an NIH stroke score, a Sepsis Score of Elebute and Stoner, a Duke Criteria for Infective Endocarditis, a Mannheim Peritonitis Index, an "Apache" score, etc.

Preferably, the methods described hereinafter utilize one or more markers that are derived from the subject. The term "subject-derived marker" as used herein refers to protein, polypeptide, phospholipid, nucleic acid, prion, glycoprotein, proteoglycan, glycolipid, lipid, lipoprotein, carbohydrate, or small molecule markers that are expressed or produced by one or more cells of the subject. The presence, absence, amount, or change in amount of one or more markers may indicate that a particular disease is present, or may indicate that a particular disease is absent. Additional markers may be used that are derived not from the subject, but rather that are expressed by pathogenic or infectious organisms that are correlated with a particular disease. Such markers are preferably protein, polypeptide, phospholipid, nucleic acid, prion, or small molecule markers that identify the infectious diseases described above. CCL23 splice variant and CCL23 are each subject-derived markers.

The term "test sample" as used herein refers to a sample of bodily fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

As used herein, a "plurality" as used herein refers to at least two. Preferably, a plurality refers to at least 3, more preferably at least 5, even more preferably at least 10, even more preferably at least 15, and most preferably at least 20. In particularly preferred embodiments, a plurality is a large number, i.e., at least 100.

The term "subject" as used herein refers to a human or non-human organism. Thus, the methods and compositions described herein are applicable to both human and veterinary disease. Further, while a subject is preferably a living organism, the invention described herein may be used in postmortem analysis as well. Preferred subjects are "patients," i.e., living humans that are receiving medical care for a disease or condition. This includes persons with no defined illness who are being investigated for signs of pathology.

The term "diagnosis" as used herein refers to methods by which the skilled artisan can estimate and/or determine whether or not a patient is suffering from a given disease or condition. It thus refers to a relative probability that a certain disease is present in the subject, and not the ability of a "specific marker" to give a definitive yes/no answer to the existence of a disease. The skilled artisan often makes a diagnosis on the basis of one or more diagnostic indicators, i.e., a marker, the presence, absence, amount, or change in amount of which is indicative of the presence, severity, or absence of the condition. The term "diagnosis" is not meant to refer to assigning the presence or absence of a particular disease or condition with absolute certainty, or even that a particular disease or condition is more likely than not. Rather, one or more markers may be used to indicate an increased or decreased risk of a particular disease or condition. For example, if CCL23 is increased above a particular level, that may indicate an increased likelihood that the subject under study suffers from sepsis, relative to a subject having a lower CCL23 level.

Similarly, the term "prognosis" refers to a relative probability that a certain future outcome will occur in the subject, and not the ability of a "specific marker" to give a definitive yes/no answer to the future outcome. A prognosis is often determined by examining one or more "prognostic indicators." These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for experiencing a future stroke in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient. Preferred prognostic markers can predict the chance of mortality in the "near term," which as used herein refers to risk within 7 days of obtaining the sample in which the prognostic indicator is measured.

The term "correlating" or "relating" as used herein in reference to the use of markers refers to comparing the presence or amount of the marker(s) in a patient to its presence or amount in persons known to suffer from, or known to be at risk of, a given condition, or in persons known to be free of a given condition, and assigning an increased or decreased probability of a particular diagnosis, prognosis, etc., to an individual based on the assay result(s) obtained from that individual. Relating an assay result to the presence or absence of a particular disease or prognosis is not meant to indicate that the assay result(s) will have a level of sensitivity and specificity that meets the ideal of 100%. Moreover, the artisan understands that markers need not be elevated in a single specific condition for such markers to be useful to the artisan in clinical diagnosis. Few, if any, such definitive tests exist.

In the simple example where an the CCL23 assays described herein are used in a univariate fashion, relating the assay results to a diagnosis or prognosis may mean comparing the measured assay result (e.g., CCL23 concentration) to a predetermined CCL23 threshold concentration arrived at by examining a population of "normal" and "diseased" subjects and selecting a threshold that provides an acceptable level of sensitivity and specificity, an acceptable odds ratio, etc. A greater probability of particular diagnosis, prognosis, etc., is assigned to the subject above the threshold, relative to that which would be assigned below the threshold. That probability may be measured qualitatively (e.g., the subject is at an increased risk of having a sepsis classification that is more severe than sepsis above the threshold than below the threshold") or quantitatively (e.g., "the odds ratio for the subject having a sepsis classification that is more severe than sepsis is 5-fold higher above the threshold than below the threshold"). Alternatively, a "quartile" approach may be used, where the probability of particular diagnosis, prognosis, etc. is assigned based on into which bin of the quartile the measured assay result falls. Numerous other ways to express the relationship of the assay results to a diagnosis or prognosis are known in the art.

A marker level in a subject's sample can be compared to a level known to be associated with a particular diagnosis. The sample's marker level is said to have been correlated with a diagnosis; that is, the skilled artisan can use the marker level to determine whether the patient likely suffers from a specific type diagnosis, and respond accordingly. Alternatively, the sample's marker level can be compared to a marker level known to be associated with a good outcome (e.g., a decreased likelihood of progressing to a more severe sepsis classification, etc.) in a "rule out" approach. In preferred embodiments, a profile of marker levels are correlated to a global probability or a particular outcome using ROC curves.

The term "discrete" as used herein refers to areas of a surface that are non-contiguous. That is, two areas are discrete from one another if a border that is not part of either area completely surrounds each of the two areas.

The term "independently addressable" as used herein refers to discrete areas of a surface from which a specific signal may be obtained.

The term "appreciable" as used herein with regard to assay signals and assay results, refers to a signal or result that is above background for a physiologically relevant concentration of an analyte.

The term "physiologically relevant concentration" as used herein refers to the average concentration of an analyte naturally present in a non-diseased subject population.

The term "therapy regimen" refers to one or more interventions made by a caregiver in hopes of treating a disease or condition. Therapy regimens for sepsis are well known in the art. Included is the "early sepsis therapy regimen," which as used herein refers to a set of supportive therapies designed to reduce the risk of mortality when administered within the initial 24 hours, more preferably within the initial 12 hours, and most preferably within the initial 6 hours or earlier, of assigning a diagnosis of SIRS, sepsis, severe sepsis, septic shock, or MODS to a subject. Such supportive therapies comprise a spectrum of treatments including resuscitation, fluid delivery, vasopressor administration, inotrope administration, steroid administration, blood product administration, and/or sedation. See, e.g., Dellinger et al., *Crit. Care Med.* 32: 858-873, 2004, and Rivers et al., *N. Engl. J. Med.* 345: 1368-1377, 2001 (providing a description of "early goal directed therapy" as that term is used herein), each of which is hereby incorporated by reference. Preferably, such an early sepsis therapy regimen comprises one or more, and preferably a plurality, of the following therapies:

maintenance of a central venous pressure of 8-12 mm Hg, preferably by administration of crystalloids and/or colloids as necessary;

maintenance of a mean arterial pressure of $\geq 65$ mm Hg, preferably by administration of vasopressors and/or vasodilators as necessary;

maintenance of a central venous oxygen saturation of $\geq 70\%$ preferably by administration of transfused red blood cells to a hematocrit of at least 30% and/or administration of dobutamine as necessary; and administration of mechanical ventilation as necessary.

The term "related marker" as used herein refers to one or more immunologically detectable fragments of a particular marker or its biosynthetic parent that comprise 8 or more contiguous residues of the marker or its parent.

For example, human BNP is derived by proteolysis of a 108 amino acid precursor molecule, referred to hereinafter as $BNP_{1-108}$. Mature BNP, or "the BNP natriuretic peptide," or "BNP-32" is a 32 amino acid molecule representing amino acids 77-108 of this precursor, which may be referred to as $BNP_{77-108}$. The remaining residues 1-76 are referred to hereinafter as $BNP_{1-76}$, and are also known as "NT-proBNP."

The sequence of the 108 amino acid BNP precursor pro-BNP ($BNP_{1-108}$) is as follows, with mature BNP ($BNP_{77-108}$) underlined:

```
                                                    (SEQ ID NO: 5)
HPLGSPGSAS DLETSGLQEQ RNHLQGKLSE LQVEQTSLEP LQESPRPTGV    50

WKSREVATEG IRGHRKMVLY TLRAPRSPKM VQGSGCFGRK MDRISSSSGL   100

GCKVLRRH.                                               108
```

$BNP_{1-108}$ is synthesized as a larger precursor pre-pro-BNP having the following sequence (with the "pre" sequence shown in bold):

```
                                                    (SEQ ID NO: 6)
MDPQTAPSRA LLLLLFLHLA FLGGRSHPLG SPGSASDLET SGLQEQRNHL    50

QGKLSELQVE QTSLEPLQES PRPTGVWKSR EVATEGIRGH RKMVLYTLRA   100

PRSPKMVQGS GCFGRKMDRI SSSSGLGCKV LRRH.                  134
```

While mature BNP itself may be used as a marker in the present invention, the prepro-BNP, $BNP_{1-108}$ and $BNP_{1-76}$ molecules represent BNP-related markers that may be measured either as surrogates for mature BNP or as markers in and of themselves. In addition, one or more fragments of these molecules, including BNP-related polypeptides selected from the group consisting of $BNP_{77-106}$, $BNP_{79-106}$, $BNP_{76-107}$, $BNP_{69-108}$, $BNP_{79-108}$, $BNP_{80-108}$, $BNP_{81-108}$, $BNP_{83-108}$, $BNP_{39-86}$, $BNP_{53-85}$, $BNP_{66-98}$, $BNP_{30-103}$, $BNP_{11-107}$, $BNP_{9-106}$, and $BNP_{3-108}$ may also be present in circulation. In addition, natriuretic peptide fragments, including BNP fragments, may comprise one or more oxidizable methionines, the oxidation of which to methionine sulfoxide or methionine sulfone produces additional BNP-related markers. See, e.g., U.S. patent Ser. No. 10/419,059, filed Apr. 17, 2003, which is hereby incorporated by reference in its entirety including all tables, figures and claims.

Because production of marker fragments is an ongoing process that may be a function of, inter alfa, the elapsed time between onset of an event triggering marker release into the tissues and the time the sample is obtained or analyzed; the elapsed time between sample acquisition and the time the sample is analyzed; the type of tissue sample at issue; the storage conditions; the quantity of proteolytic enzymes present; etc., it may be necessary to consider this degradation when both designing an assay for one or more markers, and when performing such an assay, in order to provide an accurate prognostic or diagnostic result. In addition, individual antibodies that distinguish amongst a plurality of marker fragments may be individually employed to separately detect the presence or amount of different fragments. The results of this individual detection may provide a more accurate prognostic or diagnostic result than detecting the plurality of fragments in a single assay. For example, different weighting factors may be applied to the various fragment measurements to provide a more accurate estimate of the amount of natriuretic peptide originally present in the sample.

In a similar fashion, many of the markers described herein are synthesized as larger precursor molecules, which are then processed to provide mature marker; and/or are present in circulation in the form of fragments of the marker. Thus, "related markers" to each of the markers described herein may be identified and used in an analogous fashion to that described above for BNP.

Removal of polypeptide markers from the circulation often involves degradation pathways. Moreover, inhibitors of such degradation pathways may hold promise in treatment of certain diseases. See, e.g., Trindade and Rouleau, *Heart Fail. Monit.* 2: 2-7, 2001. However, the measurement of the polypeptide markers has focused generally upon measurement of the intact form without consideration of the degradation state of the molecules. Assays may be designed with an understanding of the degradation pathways of the polypeptide markers and the products formed during this degradation, in order to accurately measure the biologically active forms of a particular polypeptide marker in a sample. The unintended measurement of both the biologically active polypeptide marker(s) of interest and inactive fragments derived from the markers may result in an overestimation of the concentration of biologically active form(s) in a sample.

The failure to consider the degradation fragments that may be present in a clinical sample may have serious consequences for the accuracy of any diagnostic or prognostic method. Consider for example a simple case, where a sandwich immunoassay is provided for BNP, and a significant amount (e.g., 50%) of the biologically active BNP that had been present has now been degraded into an inactive form. An immunoassay formulated with antibodies that bind a region common to the biologically active BNP and the inactive fragment(s) will overestimate the amount of biologically active BNP present in the sample by 2-fold, potentially resulting in a "false positive" result. Overestimation of the biologically active form(s) present in a sample may also have serious consequences for patient management. Considering the BNP example again, the BNP concentration may be used to determine if therapy is effective (e.g., by monitoring BNP to see if an elevated level is returning to normal upon treatment). The same "false positive" BNP result discussed above may lead the physician to continue, increase, or modify treatment because of the false impression that current therapy is ineffective.

Likewise, it may be necessary to consider the complex state of one or more markers described herein. For example, troponin exists in muscle mainly as a "ternary complex" comprising three troponin polypeptides (T, I and C). But troponin I and troponin T circulate in the blood in forms other than the I/T/C ternary complex. Rather, each of (i) free cardiac-specific troponin I, (ii) binary complexes (e.g., troponin I/C complex), and (iii) ternary complexes all circulate in the blood. Furthermore, the "complex state" of troponin I and T may change over time in a patient, e.g., due to binding of free troponin polypeptides to other circulating troponin polypeptides. Immunoassays that fail to consider the "complex state" of troponin may not detect all of the cardiac-specific isoform of interest.

Selecting a Threshold

The artisan understands that even for biomarkers that are routinely used in the medical setting, the performance characteristics, such as the desired specificity and sensitivity, appropriate thresholds, etc., for the particular test and patient population under study must be established by the skilled artisan. While it may seem that two assays for a particular biomarker should give the same result (that is, that 100 ng/mL is 100 ng/mL, no matter what test is being used), that is not typically the case for immunoassays.

For example, in the case of cardiac troponin I (a marker of myocardial damage commonly assayed in clinical laboratories), it has been reported that measurements using different commercial FDA-approved troponin I assays on identical specimens may differ in measured concentration by 100-fold. See, e.g., Christenson et al., "Standardization of Cardiac Troponin I Assays: Round Robin of Ten Candidate Reference Materials," *Clin. Chem.* 47: 431-37 (2001). Said another way, a threshold concentration selected for a particular assay platform may not translate to a different assay platform. Thus, in developing a particular marker test, the artisan understands that appropriate thresholds, the concentration of a particular marker in an individual, the concentration that is considered "physiologically relevant," etc., need to be determined for that particular test, and certain well established methods are often used to do so.

In one embodiment, levels of the marker(s) being employed are obtained from a group of subjects that is divided into at least two sets. The first set includes subjects who have been confirmed as having a disease, outcome, or, more generally, being in a first condition state. For example, this first set of patients may be those diagnosed with severe sepsis (diagnosis group), those that progress to a worsening sepsis category (prognosis group), or those that improve following treatment (therapy group). Subjects in this first set will be referred to as "diseased," however this label is arbitrary. The second set of subjects is simply those who do not fall within the first set. Subjects in this second set will be referred to as "non-diseased," although again this label is arbitrary. Preferably, the first set and the second set each have an approximately equal number of subjects. The second set may be normal patients, and/or patients that do not suffer from recurrence, and/or that fail to improve or worsen following treatment.

In addition, serial testing of a marker in the same patient may also be used to establish a threshold. In effect, an earlier assay result from the same patient acts as a threshold to which later results may be compared. For example, procalcitonin (PCT) has been proposed as a marker of disease severity in sepsis, and serial measurements have been suggested to monitor response to therapy. Similarly, persistently high CRP concentrations have been associated with a poor outcome, and serial measurements may be used to identify those patients who require more aggressive interventions to prevent complications, and anti-inflammatory cytokine levels such as IL-1ra reportedly remain elevated in patients that suffer from multiple organ failure, while in patients without multiple organ failure such levels decline.

As noted above, a single marker often is incapable of definitively identifying a subject as falling within a first or second group. For example, if a patient is measured as having a marker level that falls within an overlapping region in the distribution of diseased and non-diseased subjects, the results of the test may be useless in diagnosing the patient. A cutoff may be established to distinguish between a positive and a negative test result for the detection of the disease or condition. Regardless of where the cutoff is selected, the effectiveness of the single marker as a diagnosis tool is unaffected. Changing the cutoff trades off between the number of false positives and the number of false negatives resulting from the use of the single marker.

The effectiveness of a test having such an overlap is often expressed using a ROC (Receiver Operating Characteristic) curve. ROC curves are well known to those skilled in the art. The horizontal axis of the ROC curve represents (1-specificity), which increases with the rate of false positives. The vertical axis of the curve represents sensitivity, which increases with the rate of true positives. Thus, for a particular cutoff selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

Measures of test accuracy may be obtained as described in Fischer et al., *Intensive Care Med.* 29: 1043-51, 2003, and used to determine the effectiveness of a given marker or panel of markers. These measures include sensitivity and specificity, predictive values, likelihood ratios, diagnostic odds ratios, and ROC curve areas. As discussed above, preferred tests and assays exhibit one or more of the following results on these various measures:

at least 70% sensitivity,
    at least 70% specificity;
    an odds ratio of at least 3 or 0.33 or less;
    ROC curve area of at least 0.6, more preferably 0.7, still more preferably at least 0.8, even more preferably at least 0.9, and most preferably at least 0.95; and/or a positive likelihood ratio (calculated as sensitivity/(1-specificity)) of at least 5, more preferably at least 10, and most preferably at least 20, and a negative likelihood ratio (calculated as (1-sensitivity)/specificity) of less than or equal to 0.3, more preferably less than or equal to 0.2, and most preferably less than or equal to 0.1.

Use of CCL23 Assays in Combination with Other Clinical Indicia

Once obtained, the relationship of the assay results to a particular diagnosis or prognosis may be used in a variety of manners. For example, a diagnosis indicating an increased diagnostic or prognostic risk may result in sending the subject for additional diagnostic tests. An increased risk of a particular diagnosis or prognosis may be assigned to a subject based on the use of one or more CCL23 assays of the present invention by comparing a measured concentration to some cutoff. That risk may be further increased if another marker also indicates an increased risk of the same diagnosis or prognosis, or may be decreased if another marker indicates a decreased risk of the same diagnosis or prognosis. As discussed herein, markers may include subject-derived markers, but may also include clinical indicia of a patient's disease state, such as the Acute Physiology and Chronic Health Evaluation II (APACHE II) score, Elebute score, Multiple Organ Failure-Goris score, Simplified Acute Physiology Score, Sepsis Severity Score, or Mannheim Peritonitis Index (MPI). This list is not meant to be limiting.

A panel consisting of the markers referenced herein and/or their related markers may be constructed to provide relevant information related to the diagnosis of interest. Such a panel may be constructed using 1, 2, 3, 4, 5, 6, 7, 8, 9, 10, 11, 12, 13, 14, 15, 16, 17, 18, 19, 20, or more individual markers. The analysis of a single marker or subsets of markers comprising a larger panel of markers could be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity.

The following table provides a list of additional preferred markers for use in the present invention. Further detail is provided in US2005/0148029, which is hereby incorporated by reference in its entirety. As described herein, markers related to each of these markers are also encompassed by the present invention.

TABLE 6

| Marker | Classification |
| --- | --- |
| Myoglobin | Tissue injury |
| E-selectin | Tissue injury |
| VEGF | Tissue injury |
| EG-VEGF | Tissue injury |
| Troponin I and complexes | Myocardial injury |
| Troponin T and complexes | Myocardial injury |
| Annexin V | Myocardial injury |
| B-enolase | Myocardial injury |
| CK-MB | Myocardial injury |
| Glycogen phosphorylase-BB | Myocardial injury |
| Heart type fatty acid binding protein | Myocardial injury |
| Phosphoglyceric acid mutase | Myocardial injury |
| S-100ao | Myocardial injury |
| ANP | Blood pressure regulation |

TABLE 6-continued

| Marker | Classification |
| --- | --- |
| CNP | Blood pressure regulation |
| Kininogen | Blood pressure regulation |
| CGRP II | Blood pressure regulation |
| urotensin II | Blood pressure regulation |
| BNP | Blood pressure regulation |
| NT-proBNP | Blood pressure regulation |
| proBNP | Blood pressure regulation |
| calcitonin gene related peptide | Blood pressure regulation |
| arg-Vasopressin | Blood pressure regulation |
| Endothelin-1 (and/or Big ET-1) | Blood pressure regulation |
| Endothelin-2 (and/or Big ET-2) | Blood pressure regulation |
| Endothelin-3 (and/or Big ET-3) | Blood pressure regulation |
| procalcitonin | Blood pressure regulation |
| calcyphosine | Blood pressure regulation |
| adrenomedullin | Blood pressure regulation |
| aldosterone | Blood pressure regulation |
| angiotensin 1 (and/or angiotensinogen 1) | Blood pressure regulation |
| angiotensin 2 (and/or angiotensinogen 2) | Blood pressure regulation |
| angiotensin 3 (and/or angiotensinogen 3) | Blood pressure regulation |
| Bradykinin | Blood pressure regulation |
| Tachykinin-3 | Blood pressure regulation |
| calcitonin | Blood pressure regulation |
| Renin | Blood pressure regulation |
| Urodilatin | Blood pressure regulation |
| Ghrelin | Blood pressure regulation |
| Plasmin | Coagulation and hemostasis |
| Thrombin | Coagulation and hemostasis |
| Antithrombin-III | Coagulation and hemostasis |
| Fibrinogen | Coagulation and hemostasis |
| von Willebrand factor | Coagulation and hemostasis |
| D-dimer | Coagulation and hemostasis |
| PAI-1 | Coagulation and hemostasis |
| Protein C | Coagulation and hemostasis |
| Soluble Endothelial Protein C Receptor (EPCR) | Coagulation and hemostasis |
| TAFI | Coagulation and hemostasis |
| Fibrinopeptide A | Coagulation and hemostasis |
| Plasmin alpha 2 antiplasmin complex | Coagulation and hemostasis |
| Platelet factor 4 | Coagulation and hemostasis |
| Platelet-derived growth factor | Coagulation and hemostasis |
| P-selectin | Coagulation and hemostasis |
| Prothrombin fragment 1 + 2 | Coagulation and hemostasis |
| B-thromboglobulin | Coagulation and hemostasis |
| Thrombin antithrombin III complex | Coagulation and hemostasis |
| Thrombomodulin | Coagulation and hemostasis |
| Thrombus Precursor Protein | Coagulation and hemostasis |
| Tissue factor | Coagulation and hemostasis |
| Tissue factor pathway inhibitor-α | Coagulation and hemostasis |
| Tissue factor pathway inhibitor-β | Coagulation and hemostasis |
| basic calponin 1 | Vascular tissue |
| beta like 1 integrin | Vascular tissue |
| Calponin | Vascular tissue |
| CSRP2 | Vascular tissue |
| elastin | Vascular tissue |
| Endothelial cell-selective adhesion molecule (ESAM) | Vascular tissue |
| Fibrillin 1 | Vascular tissue |
| Junction Adhesion Molecule-2 | Vascular tissue |
| LTBP4 | Vascular tissue |
| smooth muscle myosin | Vascular tissue |
| transgelin | Vascular tissue |
| Carboxyterminal propeptide of type I procollagen (PICP) | Collagen synthesis |
| Collagen carboxyterminal telopeptide (ICTP) | Collagen degradation |
| APRIL (TNF ligand superfamily member 13) | Inflammatory |
| CD27 (TNFRSF7) | Inflammatory |
| Complement C3a | Inflammatory |
| CCL-5 (RANTES) | Inflammatory |
| CCL-8 (MCP-2) | Inflammatory |
| CCL-16 | Inflammatory |
| CCL-19 (macrophage inflammatory protein-3β) | Inflammatory |
| CCL-20 (MIP-3α) | Inflammatory |
| CCL-23 (MIP-3) | Inflammatory |
| CXCL-5 (small inducible cytokine B5) | Inflammatory |
| CXCL-9 (small inducible cytokine B9) | Inflammatory |
| CXCL-13 (small inducible cytokine B13) | Inflammatory |
| CXCL-16 (small inducible cytokine B16) | Inflammatory |

TABLE 6-continued

| Marker | Classification |
|---|---|
| DPP-II (dipeptidyl peptidase II) | Inflammatory |
| DPP-IV (dipeptidyl peptidase IV) | Inflammatory |
| Glutathione S Transferase | Inflammatory |
| HIF 1 ALPHA | Inflammatory |
| IL-25 | Inflammatory |
| IL-23 | Inflammatory |
| IL-22 | Inflammatory |
| IL-18 | Inflammatory |
| IL-13 | Inflammatory |
| IL-12 | Inflammatory |
| IL-10 | Inflammatory |
| IL-1-Beta | Inflammatory |
| IL-1ra | Inflammatory |
| IL-4 | Inflammatory |
| IL-6 | Inflammatory |
| IL-8 | Inflammatory |
| Lysophosphatidic acid | Inflammatory |
| MDA-modified LDL | Inflammatory |
| Human neutrophil elastase | Inflammatory |
| C-reactive protein | Inflammatory |
| Insulin-like growth factor | Inflammatory |
| Inducible nitric oxide synthase | Inflammatory |
| Intracellular adhesion molecule | Inflammatory |
| NGAL (Lipocalin-2) | Inflammatory |
| Lactate dehydrogenase | Inflammatory |
| MCP-1 | Inflammatory |
| MMP-1 | Inflammatory |
| MMP-2 | Inflammatory |
| MMP-3 | Inflammatory |
| MMP-7 | Inflammatory |
| MMP-9 | Inflammatory |
| TIMP-1 | Inflammatory |
| TIMP-2 | Inflammatory |
| TIMP-3 | Inflammatory |
| NGAL | Inflammatory |
| n-acetyl aspartate | Inflammatory |
| PTEN | Inflammatory |
| Phospholipase A2 | Inflammatory |
| TNF Receptor Superfamily Member 1A | Inflammatory |
| TNFRSF3 (lymphotoxin β receptor) | Inflammatory |
| Transforming growth factor beta | Inflammatory |
| TREM-1 | Inflammatory |
| TREM-1sv | Inflammatory |
| TL-1 (TNF ligand related molecule-1) | Inflammatory |
| TL-1a | Inflammatory |
| Tumor necrosis factor alpha | Inflammatory |
| Vascular cell adhesion molecule | Inflammatory |
| Vascular endothelial growth factor | Inflammatory |
| cystatin C | Inflammatory |
| substance P | Inflammatory |
| Myeloperoxidase (MPO) | Inflammatory |
| macrophage inhibitory factor | Inflammatory |
| Fibronectin | Inflammatory |
| cardiotrophin 1 | Inflammatory |
| Haptoglobin | Inflammatory |
| PAPPA | Inflammatory |
| s-CD40 ligand | Inflammatory |
| HMG-1 (or HMGB1) | Inflammatory |
| IL-2 | Inflammatory |
| IL-4 | Inflammatory |
| IL-11 | Inflammatory |
| IL-13 | Inflammatory |
| IL-18 | Inflammatory |
| Eosinophil cationic protein | Inflammatory |
| Mast cell tryptase | Inflammatory |
| VCAM | Inflammatory |
| sICAM-1 | Inflammatory |
| TNFα | Inflammatory |
| Osteoprotegerin | Inflammatory |
| Prostaglandin D-synthase | Inflammatory |
| Prostaglandin E2 | Inflammatory |
| RANK ligand | Inflammatory |
| RANK (TNFRSF11A) | Inflammatory |
| HSP-60 | Inflammatory |
| Serum Amyloid A | Inflammatory |
| s-iL 18 receptor | Inflammatory |
| S-iL-1 receptor | Inflammatory |
| s-TNF P55 | Inflammatory |
| s-TNF P75 | Inflammatory |
| sTLR-1 (soluble toll-like receptor-1) | Inflammatory |
| sTLR-2 | Inflammatory |
| sTLR-4 | Inflammatory |
| TGF-beta | Inflammatory |
| MMP-11 | Inflammatory |
| Beta NGF | Inflammatory |
| CD44 | Inflammatory |
| EGF | Inflammatory |
| E-selectin | Inflammatory |
| Fibronectin | Inflammatory |
| RAGE | Inflammatory |
| Neutrophil elastase | Pulmonary injury |
| KL-6 | Pulmonary injury |
| LAMP 3 | Pulmonary injury |
| LAMP3 | Pulmonary injury |
| Lung Surfactant protein A | Pulmonary injury |
| Lung Surfactant protein B | Pulmonary injury |
| Lung Surfactant protein C | Pulmonary injury |
| Lung Surfactant protein D | Pulmonary injury |
| phospholipase D | Pulmonary injury |
| PLA2G5 | Pulmonary injury |
| SFTPC | Pulmonary injury |
| MAPK10 | Neural tissue injury |
| KCNK4 | Neural tissue injury |
| KCNK9 | Neural tissue injury |
| KCNQ5 | Neural tissue injury |
| 14-3-3 | Neural tissue injury |
| 4.1B | Neural tissue injury |
| APO E4-1 | Neural tissue injury |
| myelin basic protein | Neural tissue injury |
| Atrophin 1 | Neural tissue injury |
| Brain derived neurotrophic factor | Neural tissue injury |
| Brain fatty acid binding protein | Neural tissue injury |
| Brain tubulin | Neural tissue injury |
| CACNA1A | Neural tissue injury |
| Calbindin D | Neural tissue injury |
| Calbrain | Neural tissue injury |
| Carbonic anhydrase XI | Neural tissue injury |
| CBLN1 | Neural tissue injury |
| Cerebellin 1 | Neural tissue injury |
| Chimerin 1 | Neural tissue injury |
| Chimerin 2 | Neural tissue injury |
| CHN1 | Neural tissue injury |
| CHN2 | Neural tissue injury |
| Ciliary neurotrophic factor | Neural tissue injury |
| CK-BB | Neural tissue injury |
| CRHR1 | Neural tissue injury |
| C-tau | Neural tissue injury |
| DRPLA | Neural tissue injury |
| GFAP | Neural tissue injury |
| GPM6B | Neural tissue injury |
| GPR7 | Neural tissue injury |
| GPR8 | Neural tissue injury |
| GRIN2C | Neural tissue injury |
| GRM7 | Neural tissue injury |
| HAPIP | Neural tissue injury |
| HIP2 | Neural tissue injury |
| LDH | Neural tissue injury |
| Myelin basic protein | Neural tissue injury |
| NCAM | Neural tissue injury |
| NT-3 | Neural tissue injury |
| NDPKA | Neural tissue injury |
| Neural cell adhesion molecule | Neural tissue injury |
| NEUROD2 | Neural tissue injury |
| Neurofilament L | Neural tissue injury |
| Neuroglobin | Neural tissue injury |
| neuromodulin | Neural tissue injury |
| Neuron specific enolase | Neural tissue injury |
| Neuropeptide Y | Neural tissue injury |
| Neurotensin | Neural tissue injury |
| Neurotrophin 1,2,3,4 | Neural tissue injury |
| NRG2 | Neural tissue injury |
| PACE4 | Neural tissue injury |
| phosphoglycerate mutase | Neural tissue injury |
| PKC gamma | Neural tissue injury |
| proteolipid protein | Neural tissue injury |
| PTEN | Neural tissue injury |

TABLE 6-continued

| Marker | Classification |
| --- | --- |
| PTPRZ1 | Neural tissue injury |
| RGS9 | Neural tissue injury |
| RNA Binding protein Regulatory Subunit | Neural tissue injury |
| s-100β | Neural tissue injury |
| SCA7 | Neural tissue injury |
| secretagogin | Neural tissue injury |
| SLC1A3 | Neural tissue injury |
| SORL1 | Neural tissue injury |
| SREB3 | Neural tissue injury |
| STAC | Neural tissue injury |
| STX1A | Neural tissue injury |
| STXBP1 | Neural tissue injury |
| Syntaxin | Neural tissue injury |
| thrombomodulin | Neural tissue injury |
| transthyretin | Neural tissue injury |
| adenylate kinase-1 | Neural tissue injury |
| BDNF | Neural tissue injury |
| neurokinin A | Neural tissue injury |
| neurokinin B | Neural tissue injury |
| s-acetyl Glutathione | apoptosis |
| cytochrome C | apoptosis |
| Caspase 3 | apoptosis |
| Cathepsin D | apoptosis |
| α-spectrin | apoptosis |

Preferred panels comprise combining a CCL23 splice variant assay and/or total CCL23 assay with one or more additional immunoassays that detect markers selected from the group consisting of NT-proBNP, proBNP, $BNP_{79-108}$, BNP, $BNP_{3-108}$, CCL23 (CCL23-specific), CRP, D-dimer, IL-1ra, NGAL, peptidoglycan recognition protein, procalcitonin, $procalcitonin_{3-116}$, active protein C, latent protein C, total protein C, and sTNFR1a. Particularly preferred panels comprise combining a CCL23 splice variant assay and/or total CCL23 assay with one or more of a CCL23-specific assay, an NGAL assay, and a CRP assay. Most preferred panels comprise combining a CCL23 splice variant assay and/or total CCL23 assay with an NGAL assay, and a CRP assay.

One skilled in the art will also recognize that univariate analysis of markers can be performed and the data from the univariate analyses of multiple markers can be combined to form panels of markers to differentiate different disease conditions. Such methods include multiple linear regression, determining interaction terms, stepwise regression, etc. In preferred embodiments, marker panels combine multiple marker assay results into a single composite result. This single composite result may be used as if it is a single marker, and so subjected to ROC analysis to select decision thresholds, etc. Suitable methods for identifying and using markers panels are described in detail in U.S. Provisional Patent Application No. 60/436,392 filed Dec. 24, 2002, PCT application US03/41426 filed Dec. 23, 2003, U.S. patent application Ser. No. 10/331,127 filed Dec. 27, 2002, and PCT application No. US03/41453, each of which is hereby incorporated by reference in its entirety, including all tables, figures, and claims.

Clinical and marker data may also be combined using classification trees (also known as decision trees). Many statistical software packages are available that will implement this given the clinical data in the format X(m,n) and R(n). For example, MATLAB, or CART, or SPSS, etc. The trees may be produced with a large variety of splitting rules, prior probabilities, and weighting schemes. The trees may be fit to an arbitrary level of detail, or pruned using various cross-validation methods to avoid over-fitting the data. Large ensembles of trees may also be combined, for example, via Bootstrap Aggregation. A multivariate logistic regression model may be fed as input (together with the biomarkers) to a decision tree algorithm, or vice versa, the node assignments of a decision tree model may be fed as input (together with the biomarkers) into multivariate logistic regression. Similarly, any of the models may be fed as one of the inputs (together with the biomarkers) to a Neural Network.

Selecting and Monitoring a Treatment Regimen

Just as the potential causes of any particular nonspecific symptom may be a large and diverse set of conditions, the appropriate treatments for these potential causes may be equally large and diverse. However, once a diagnosis is obtained, the clinician can readily select a treatment regimen that is compatible with the diagnosis. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. With regard to SIRS, sepsis, severe sepsis, and septic shock, recent guidelines provide additional information for the clinician. See, e.g., Dellinger et al., Crit. Care Med. 32: 858-73, 2004, which is hereby incorporated by reference in its entirety.

Primary treatments available to US clinicians are antibiotics and intensive care support such as ventilators and hemodialysis in cases of organ failure. Recent advances are leading to improvements in how severe sepsis patients are treated. Xigris (drotrecogin alfa [activated], also known as activated Protein C) has found use in cases of severe sepsis. The following treatments can be included in a sepsis therapy regimen:

Administration of intravenous antibiotic therapy;
maintenance of a central venous pressure of 8-12 mm Hg;
administration of crystalloids and/or colloids, preferably to maintain such a central venous pressure;
maintenance of a mean arterial pressure of ≧65 mm Hg;
administration of one or more vasopressors (e.g., norepinephrine, dopamine, and/or vasopressin) and/or vasodilators (e.g., prostacyclin, pentoxifylline, N-acetyl-cysteine);
administration of one or more corticosteroids (e.g., hydrocortisone);
administration of recombinant activated protein C;
maintenance of a central venous oxygen saturation of ≧70%;
administration of transfused red blood cells to a hematocrit of at least 30%;
administration of one or more inotropics (e.g., dobutamine); and
administration of mechanical ventilation.

This list is not meant to be limiting. In addition, since the methods and compositions described herein provide prognostic information, the panels and markers of the present invention may be used to monitor a course of treatment. For example, improved or worsened prognostic state may indicate that a particular treatment is or is not efficacious.

Assay Measurement Strategies

Numerous methods and devices are well known to the skilled artisan for the detection and analysis of the markers of the instant invention. With regard to polypeptides or proteins in patient test samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. For separate or sequential assay of markers, suitable apparatuses include clinical laboratory analyzers such as the ELECSYS® (Roche), the AXSYM® (Abbott), the ACCESS® (Beckman), the ADVIA® CENTAUR® (Bayer) immunoassay systems, the NICHOLS ADVANTAGE® (Nichols Institute) immunoassay system, etc.

Preferably the markers are analyzed using an immunoassay, and most preferably sandwich immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

Preferred apparatuses perform simultaneous assays of a plurality of markers using a single test device. Particularly useful physical formats comprise surfaces having a plurality of discrete, addressable locations for the detection of a plurality of different analytes. Such formats include protein microarrays, or "protein chips" (see, e.g., Ng and Ilag, *J. Cell Mol. Med.* 6: 329-340 (2002)) and certain capillary devices (see, e.g., U.S. Pat. No. 6,019,944). In these embodiments, each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection.

The use of immobilized antibodies specific for the markers is also contemplated by the present invention. The antibodies could be immobilized onto a variety of solid phase supports, such as magnetic or chromatographic matrix particles, the surface of an assay place (such as microtiter wells), pieces of a solid substrate material or membrane (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

Particularly preferred assay devices of the present invention will comprise, for one or more assays, a first antibody conjugated to a solid phase and a second antibody conjugated to a signal development element. Such assay devices are configured to perform a sandwich immunoassay for one or more analytes. These assay devices will preferably further comprise a sample application zone, and a flow path from the sample application zone to a second device region comprising the first antibody conjugated to a solid phase.

Flow of a sample along the flow path may be driven passively (e.g., by capillary, hydrostatic, or other forces that do not require further manipulation of the device once sample is applied), actively (e.g., by application of force generated via mechanical pumps, electroosmotic pumps, centrifugal force, increased air pressure, etc.), or by a combination of active and passive driving forces. Most preferably, sample applied to the sample application zone will contact both a first antibody conjugated to a solid phase and a second antibody conjugated to a signal development element along the flow path (sandwich assay format). Additional elements, such as filters to separate plasma or serum from blood, mixing chambers, etc., may be included as required by the artisan. Exemplary devices are described in Chapter 41, entitled "Near Patient Tests: TRIAGE® Cardiac System," in *The Immunoassay Handbook*, $2^{nd}$ ed., David Wild, ed., Nature Publishing Group, 2001, which is hereby incorporated by reference in its entirety.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

A panel consisting of the markers referenced above may be constructed to provide relevant information related to differential diagnosis. Such a panel may be constructed using 1, 2, 3, 4, 5, 6, 7, 8, 9, 10, 15, 20, or more individual markers. The analysis of a single marker or subsets of markers comprising a larger panel of markers could be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, $2^{nd}$ edition, Carl Burtis and Edward Ashwood eds., W.B. Saunders and Company, p. 496).

The present invention also provides a kit for the analysis of markers. Such a kit preferably comprises devises and reagents for the analysis of at least one test sample and instructions for performing the assay. Optionally the kits may contain one or more means for using information obtained from immunoassays performed for a marker panel to rule in or out certain diagnoses. This can include instructions and/or parameters on a computer-readable medium for use (i) in correlating assay results to a positive and/or negative result for the diagnoses, prognoses, etc., described herein; and/or (ii) lot specific information, such as standard curves, expiration dates, etc. Other measurement strategies applicable to the methods described herein include chromatography (e.g., HPLC), mass spectrometry, receptor-based assays, and combinations of the foregoing.

A computer readable storage medium, for example, one or more solid state memory devices (ROM chips or other removable chip-based memories), removable computer disks, magnetic strips, RFID-type inductive labels, bar codes, etc., can be provided in the kit to deliver test-related information and data to a computer processor used with the immunoassay device(s). In addition to operating instructions, such storage media can also be used to provide other pertinent data to a computer processor to be used in controlling and calibrating the tests to be performed. For example, test software can include program instructions and/or parameters used to direct the performance of one or more assays and correlations, as described herein. This may include calibration curves utilized to perform the desired test, test software, expiration dates, as well as other program information and calibration and control information for the instrument. In the case where the CCL23 assays are used in a univariate manner, this may include one or more thresholds used to assign likelihood of a diagnosis or prognosis, based on an assay result. In the case of multivariate analyses, this may include parameters used to combine the results of multiple markers, and some threshold(s) to which the combined result is compared for assigning the likelihood of a diagnosis or prognosis.

Selection of Antibodies

The generation and selection of antibodies may be accomplished several ways. For example, one way is to purify polypeptides of interest or to synthesize the polypeptides of interest using, e.g., solid phase peptide synthesis methods well known in the art. See, e.g., *Guide to Protein Purification*, Murray P. Deutcher, ed., *Meth. Enzymol.* Vol 182 (1990); Solid Phase Peptide Synthesis, Greg B. Fields ed., *Meth. Enzymol. Vol* 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be injected, for example, into mice or rabbits, to generate polyclonal or monoclonal antibodies. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; *J. Immunol.* 149, 3914-3920 (1992)).

In addition, numerous publications have reported the use of phage display technology to produce and screen libraries of polypeptides for binding to a selected target. See, e.g., Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

EXAMPLES

The following examples serve to illustrate the present invention. These examples are in no way intended to limit the scope of the invention.

Example 1

CCL23 Assay Design

As noted above, CCL23 splice variant differs from CCL23 by replacement of $R_{46}$ by MLWRRKIGPQMTLSHAAG (SEQ ID NO:3), represented by underlining in the following sequence of the mature CCL23 protein (that is, with the signal sequence deleted):

```
                                                         (SEQ ID NO: 1)
        10         20         30         40         50         60
RVTKDAETEF MMSKLPLENP VLLDMLWRRK IGPQMTLSHA AGFHATSADC CISYTPRSIP 70         80         90        100        110        116
CSLLESYFET NSECSKPGVI FLTKKGRRFC ANPSDKQVQV CMRMLKLDTR IKTRKN.
```

In addition, certain N-terminally truncated forms are believed generated by cleavage of the mature CCL23 protein in rheumatoid arthritis. See, e.g., Berahovich et al, *J. Immunol.* 174: 7341-51, 2005.

The following assays were designed:

Assay 1: A "total" CCL23 assay using two antibodies that paired in a sandwich format, and were each directed to an epitope C-terminal to the splice variant insertion and common to both CCL23 and CCL23 splice variant. This assay recognizes the major N-terminal processed form of CCL23 ($CCL23_{22-99}$) generated by elastase cleavage of CCL23 and the corresponding truncated form of CCL23 splice variant if it exists.

Assay 2: A "full length" CCL23 assay using two antibodies that paired in a sandwich format, one of which is directed to the portion of CCL23 missing from the N-terminal processed $CCL23_{19-99}$, $CCL23_{22-99}$, $CCL23_{27-99}$, and $CCL23_{30-99}$ forms, and the second of which is directed to an epitope C-terminal to the splice variant insertion and common to both CCL23 and CCL23 splice variant. This assay does not recognize the major N-terminal processed form of CCL23 ($CCL23_{22-99}$) generated by elastase cleavage of CCL23, or the corresponding truncated forms of CCL23 splice variant if they exist. Accordingly, this assay is a "full length CCL23 immunoassay" as that term is defined above.

Assay 3: A CCL23 splice variant assay using two antibodies that paired in a sandwich format, one antibody specific for the splice variant insert, and one antibody directed to the C-terminal region common to both CCL23 and CCL23 splice variant. This assay recognizes the major N-terminal processed form of CCL23 ($CCL23_{22-99}$) generated by elastase cleavage of CCL23 and the corresponding truncated form of CCL23 splice variant if it exists. Accordingly, this assay is a "CCL23 splice variant immunoassay" as that term is defined above.

Assay 4: A CCL23-specific assay using two antibodies that paired in a sandwich format, one antibody specific for CCL23, and one antibody directed to the C-terminal region common to both CCL23 and CCL23 splice variant. This assay does not recognize CCL23 splice variant, or the major N-terminal processed form of CCL23 ($CCL23_{22-99}$) generated by elastase cleavage of CCL23, or the corresponding truncated forms of CCL23 splice variant if they exist, nor does it recognize CCL23 splice variant.

Assay 5: An assay specific for N-terminally truncated $CCL23_{22-99}$ using two antibodies that paired in a sandwich format, one antibody specific for CCL23, and one antibody directed to the truncated site. This assay does not recognize CCL23 splice variant.

Assay 6: An assay specific for N-terminally truncated $CCL23_{25-99}$ using two antibodies that paired in a sandwich format, one antibody specific for CCL23, and one antibody directed to the truncated site. This assay does not recognize CCL23 splice variant.

Antibodies common to the CCL23 and CCL23 splice variant proteins were selected from antibody phage libraries generated from spleens of mice immunized with the CCL23 protein obtained from Cell Sciences, Canton, Mass.

The splice variant specific antibody was selected from antibody phage libraries generated from the spleens of mice immunized with the peptide MLWRRKIGPQMTLSHAAGC (SEQ ID NO:7) obtained from Biopeptide, San Diego, Calif. and conjugated to KLH. This corresponds to the sequence of the splice variant insert with an additional C-terminal cysteine through which the conjugation occurs.

The CCL23-specific antibody was selected from antibody phage libraries generated from the spleens of mice immunized with the peptide RFHATSADC (SEQ ID NO: 8) obtained from Biopeptide, San Diego, Calif.) and conjugated to KLH.

For antibodies specific to truncated forms, antibodies were selected from antibody phage libraries generated from spleens of mice immunized with the CCL23 protein. Panning was performed using biotinylated truncated forms in the presence of excess uncleaved CCL23 to remove antibodies that would bind the full length protein. To obtain the truncated forms, CCL23 and the CCL23 splice variant were each digested by mixing 50 µL of 0.5 mg/mL CCL23 or the splice variant in 50 µL of 100 mM Tris pH7.5, 20 mM $CaCl_2$, and 2 µL of 1 µg/µL (0.004 Unit/µL) elastase and incubating for 1-2 hours at room temperature.

Example 2

Immunization of Mice with Antigens and Purification of RNA from Mice

Ten C57 mice (Charles River Laboratories, Wilmington, Mass.) are immunized by subcutaneous administration of 50 µg of immunogen mixed with 15 µg of Quil A adjuvant (Accurate Chemical and Scientific Corp, Westbury, N.Y.) in PBS, pH 7.4 on day 0. A subsequent immunization is performed on day 14 using the immunogen mixed with Quil A. On day 23, blood samples are obtained from the mice by retro-orbital plexus bleeds and serum IgG responses are determined by ELISA using biotinylated immunogen immobilized in separate wells via neutravidin (Reacti-Bind™ NeutrAvidin™-Coated Polystyrene Plates, Pierce, Rockford, Ill.). Five of the mice (group A) are given two consecutive boosts of 50 µg of immunogen administered via intraperitoneal injection on days 29 and 30. On day 32, these mice are sacrificed and spleens are harvested for RNA isolation as described below. A third immunization is performed on the remaining five mice (group B) on day 28 using the antigen mixed with Quil A. On day 37, blood samples are obtained and serum IgG responses determined as described above. Two consecutive boosts of 50 µg of immunogen are administered via intraperitoneal injection on days 42 and 43. On day 45, the mice are sacrificed.

Spleens are harvested, macerated, then added to a polypropylene tube containing 3 mL of lysis Buffer (RA1 Buffer, Macherey-Nagel) and homogenized for 1 min using a rotostator homogenizer (Omni International). The lysates are added to wells of a Nucleospin Robot-96 RNA plate (Macherey-Nagel) and total RNA purified using a Tecan Genesis Workstation (Tecan).

Example 3

Enrichment of Polyclonal Antibody Phage

Antibody phage are generally prepared as described in WO 03/068956, the contents of which are incorporated by reference herein in their entirety, including all tables, figures, and claims, from mice immunized with as described above using BS60 uracil template. Antibody phage samples are panned with avidin magnetic latex generally as described in Example 16 of U.S. Pat. No. 6,057,098. Nucleic acids from enriched antibody phage samples are subcloned into a plasmid expression vector and electroporated into *E. coli* to generate antibody libraries as generally described in WO 03/068956.

Example 4

Selection of Monoclonal Sandwich Pairs

Antibody libraries are streaked on separate agar plates. Colonies expressing monoclonal antibodies from each library are picked to inoculate 96-well block cultures and grown overnight in at 37° C. A semi-defined culture medium (Pack, P. et al., *Bio/Technology* 11: 1271-1277, 1993, supplemented with 0.3 g/L L-leucine, 0.3 g/L L-isoleucine, 12 g/L casein enzymatic hydrolysate (ICN Biomedicals, Costa Mesa, Calif.), 12.5 g/L glycerol, and 10 μg/mL tetracycline) is used for growth of the block cultures and subsequent scale-up cultures. Aliquots of the overnight cultures are used to generate frozen cell banks, and to start serial replicate 96-well block cultures to express and purify the antibodies as generally described in WO 03/068956.

Purified antibodies are assayed for functional positives as follows: wells in Neutravidin plates (Pierce) are incubated with biotinylated target polypeptide for 1 hour at room temperature and washed. The wells are incubated with the purified antibodies for 1 hour at room temperature, washed, and incubated with Goat Anti-Mouse Kappa-Alkaline Phosphatase (Southern Biotechnolgy Associates) for 1 hour at room temperature. After a final wash, Attophos substrate solution (Promega) is added to the wells to generate kinetic fluorescent signals that are measured in a plate reader. The signals are used to identify and characterize which antibodies had been functionally captured in the wells. Select antibodies are scaled-up in shake flask cultures and purified.

Aliquots of these purified antibodies are biotinylated for use as detect antibodies to screen for sandwich antibody partners as follows. The purified antibodies in 96-well blocks are incubated overnight at 4° C. in replicate wells in high-binding plates (Nunc) to serve as capture antibodies. The wells are subsequently incubated with blocking buffer for 1 hour at room temperature and washed. The replicate wells are incubated with either unlabeled target polypeptide or buffer alone for 1 hour at room temperature and washed. Biotinylated detection antibodies are incubated in the replicate wells for 1 hour at room temperature and washed. The wells are incubated with Neutravidin-Alkaline Phosphatase (Southern Biotechnology Associates) for 1 hour at room temperature, washed, and Attophos substrate solution added to the wells to generate kinetic fluorescent signals that are measured in a plate reader. The relative signals in the replicate wells incubated with target polypeptide and buffer alone are used to identify and characterize which capture antibodies had formed a positive sandwich assay with the biotinylated detect antibodies. Based on this screen, selected antibodies are scaled-up in shake flasks and purified.

Example 5

Subject Population and Sample Collection

Test subjects in disease categories were enrolled as part of a prospective sepsis study conducted by Biosite Incorporated at 10 clinical sites in the United States. Enrollment criteria were: age 18 or older and presenting with two or more SIRS criteria, and confirmed or suspected infection and/or lactate levels greater than 2.5 mmol/L. Exclusion criteria were: pregnancy, cardiac arrest, and patients under Do Not Resuscitate (DNR) orders. Samples were collected by trained personnel in standard blood collection tubes with EDTA as the anticoagulant. The plasma was separated from the cells by centrifugation, frozen, and stored at −20° C. or colder until analysis. The plasma was frozen within 1 hour. Clinical histories are available for each of the patients to aid in the statistical analysis of the assay data. Patients were assigned a final diagnosis by a physician at the clinical site using the standard medical criteria in use at each clinical site. Patients were diagnosed as having systemic inflammatory response syndrome (SIRS), sepsis, severe sepsis, septic shock or multiple organ dysfunction syndrome (MODS).

Samples from apparently healthy blood donors were purchased from Golden West Biologicals, Inc., Temecula, Calif., and were collected according to a defined protocol. Samples were collected from normal healthy individuals with no current clinical suspicion or evidence of disease. Blood was collected by trained personnel in standard blood collection tubes with EDTA as the anticoagulant. The plasma was separates from the cells by centrifugation, frozen, and stored at −20 C or colder until analysis.

Example 6

Immunoassays

In general, for a sandwich immunoassay in microtiter plates, a monoclonal antibody directed against a selected analyte is biotinylated using N-hydroxysuccinimide biotin (NHS-biotin) at a ratio of about 5 NHS-biotin moieties per antibody. The antibody-biotin conjugate is then added to wells of a standard avidin 384 well microtiter plate, and antibody conjugate not bound to the plate is removed. This forms the "anti-marker" in the microtiter plate. Another monoclonal antibody directed against the same analyte is conjugated to alkaline phosphatase, for example using succinimidyl 4-[N-maleimidomethyl]-cyclohexane-1-carboxylate (SMCC) and N-succinimidyl 3-[2-pyridyldithio]propionate (SPDP) (Pierce, Rockford, Ill.).

Biotinylated antibodies are pipetted into microtiter plate wells previously coated with avidin and incubated for 60 min. The solution containing unbound antibody is removed, and the wells washed with a wash buffer, consisting of 20 mM borate (pH 7.42) containing 150 mM NaCl, 0.1% sodium azide, and 0.02% TWEEN®-20 surface active agent (ICI Americas). The plasma samples (e.g., 10 μL-20 μL) containing added HAMA inhibitors are pipetted into the microtiter plate wells, and incubated for 60 min. The sample is then removed and the wells washed with a wash buffer. The antibody-alkaline phosphatase conjugate is then added to the wells and incubated for an additional 60 min, after which time, the antibody conjugate is removed and the wells washed with a wash buffer. A substrate, (ATTOPHOS®, Promega, Madison, Wis.) is added to the wells, and the rate of formation of the fluorescent product is related to the concentration of the analyte in the sample tested.

For competitive immunoassays in microtiter plates, a murine monoclonal antibody directed against a selected analyte is added to the wells of a microtiter plate and immobilized by binding to goat anti-mouse antibody that is pre-absorbed to the surface of the microtiter plate wells (Pierce, Rockford, Ill.). Any unbound murine monoclonal antibody is removed after a 60 minute incubation. This forms the "anti-marker" in the microtiter plate. A purified polypeptide that is either the same as or related to the selected analyte, and that can be bound by the monoclonal antibody, is biotinylated as described above for the biotinylation of antibodies. This biotinylated polypeptide is mixed with the sample in the presence of HAMA inhibitors (human anti-mouse antibodies, or HAMA, are human immunoglobulins with specificity for mouse immunoglobulins; HAMA inhibitors may be used to reduce or eliminate false signals from these human immunoglobulins; see, e.g., Reinsberg, *Clin. Biochem,* 29:145-48, 1996), forming a mixture containing both exogenously added biotinylated polypeptide and any unlabeled analyte molecules endogenous to the sample. The amount of the monoclonal antibody and biotinylated marker added depends on various factors and is titrated empirically to obtain a satisfactory dose-response curve for the selected analyte.

This mixture is added to the microtiter plate and allowed to react with the murine monoclonal antibody for 120 minutes. After the 120 minute incubation, the unbound material is removed, and Neutralite-Alkaline Phosphatase (Southern Biotechnology; Birmingham, Ala.) is added to bind to any immobilized biotinylated polypeptide. Substrate (as described above) is added to the wells, and the rate of formation of the fluorescent product was related to the amount of biotinylated polypeptide bound, and therefore is inversely related to the endogenous amount of the analyte in the specimen.

Example 7

CCL23 Assays

For each assay, the specific biotinylated anti-CCL23 antibody (primary antibody) diluted into assay buffer (10 mM Tris, 150 mM NaCl, 1% BSA) to 2 µg/mL was added to a 384 Neutravidin coated plate (Pierce Product #NC19658) and allowed to incubate at room temperature for 1 hour. Wells were washed with wash buffer (20 mM Borate, 150 mM NaCl, 0.2% TWEEN® 20 surface active agent (ICI Americas)) and then samples and standards were added and allowed to incubate at room temperature for 1 hour. Wells again were washed and then specific fluorsceinated anti-CCL23 antibody (secondary antibody) diluted in assay buffer to 2 µg/mL was added and allowed to incubate at room temperature for 1 hour. Wells again were washed. Added anti-fluorscein antibody conjugated to alkaline phosphatase, diluted 1/2338 into assay buffer was added and allowed to incubate at room temperature for 1 hour. Finally substrate (Promega ATTOPHOS®) was added and plate was read immediately. All additions were 10 µL/well unless otherwise stated. The plates were washed 3 times between each addition, with 9 final washes.

Standards were prepared by spiking various specific forms of CCL23 antigens into a normal EDTA plasma patient pool at concentrations ranging from 0.39 to 12.5 ng/mL, including a neutralized 0, which is the EDTA plasma pool with excess concentration of each antibody used in the ELISA. Reading was performed using a Tecan Spectrafluor plus using in kinetic mode over 6 read cycles with excitation filter of 430 nm and an emission filter 570 nm. Slope of RFU/seconds was determined.

Example 8

Results

Samples were obtained 3 hrs after the time of enrollment in the study described above to identify subjects at an increased risk for progression to sepsis, severe sepsis, or septic shock, and in-hospital mortality. Patients were classified into groups as follows in Table 1. The categories EA and AS together are referred to herein by the term "advanced sepsis."

TABLE 1

| Category | Description |
|---|---|
| Normal | Banked samples from normal healthy donors. |
| SL | Patients enrolled in the study with low risk infection (or no infection) and with 2 or more SIRS criteria upon presentation to the ED. |
| ES | Patients with a high risk infection and 2 or more SIRS criteria, but not meeting the criteria for Severe Sepsis, or Septic Shock within 72 hrs of presentation to the ED. |
| EA | Patients that did not meet the criteria for Severe Sepsis, or Septic Shock upon presentation to the ED, but advanced to meet these criteria within 72 hrs. |
| AS | Patients meeting the criteria for Severe Sepsis, or Septic Shock upon presentation to the ED. |
| Alive | Patients in categories ES, EA, or AS who did not die in the hospital. |
| Dead | Patients in categories ES, EA, or AS who died in the hospital. |

The data was analyzed using standard Receiver Operator Characteristic (ROC) analysis for the case discrimination criteria shown in Table 2. "N" refers to the number of individuals in a respective category.

TABLE 2

| Criteria (written as Category(0) vs. Category(1)) | N Category(0) | N Category(1) | Description of comparison |
|---|---|---|---|
| Alive vs. Dead | 108 | 47 | Risk of death in patients with Sepsis. |
| EA vs. AS | 36 | 83 | Risk of progression to Severe Sepsis, or Septic Shock in patients with Sepsis. |
| ES + EA vs. AS | 72 | 83 | Risk of progression to Severe Sepsis, or Septic Shock in patients with Sepsis. |
| ES vs. EA | 36 | 36 | Risk of progression to Severe Sepsis, or Septic Shock in patients with Sepsis. |
| SL + ES vs. EA + AS | 140 | 119 | Risk of Progression to Sepsis |
| SL vs. AS | 104 | 83 | Diagnosis of Severe Sepsis, or Septic Shock |
| SL vs. ES + EA + AS | 104 | 155 | Risk of Progression to Sepsis |
| SL vs. ES + EA | 104 | 72 | Risk of Progression to Sepsis |
| SL vs. ES | 104 | 36 | Risk of Progression to Sepsis |
| Normal vs. ES + EA + AS | 23 | 155 | Diagnosis of Sepsis |

ROC AUC (area under the curve) were calculated for each of the assays (numbered as in Example 1 above) in each of the discrimination criteria. The statistical significance of each ROC AUC was calculated assuming a null hypothesis that the true ROC AUC is 0.5 (which is the ROC AUC of a random test, i.e., an assay that has no ability to discriminate the criteria). P values for statistical significance were calculated using a standard Z-test. A result was significant if $p \leq 0.05$; NS refers to results that were not significant. The results are shown in Tables 3 and 4.

TABLE 3

| Criteria | ROC Area for Assay | | | | | |
|---|---|---|---|---|---|---|
| | Assay 2 | Assay 4 | Assay 5 | Assay 6 | Assay 3 | Assay 1 |
| Alive vs. Dead | 0.57 | 0.55 | 0.47 | 0.44 | 0.60 | 0.60 |
| EA vs. AS | 0.59 | 0.58 | 0.52 | 0.51 | 0.65 | 0.63 |
| ES + EA vs. AS | 0.63 | 0.63 | 0.48 | 0.47 | 0.68 | 0.68 |
| ES vs. EA | 0.55 | 0.59 | 0.42 | 0.42 | 0.54 | 0.57 |
| SL + ES vs. EA + AS | 0.75 | 0.77 | 0.51 | 0.47 | 0.79 | 0.80 |
| SL vs. AS | 0.81 | 0.84 | 0.54 | 0.49 | 0.87 | 0.87 |
| SL vs. ES | 0.72 | 0.72 | 0.60 | 0.56 | 0.71 | 0.74 |
| SL vs. ES + EA | 0.73 | 0.74 | 0.56 | 0.52 | 0.72 | 0.76 |
| SL vs. ES + EA + AS | 0.77 | 0.79 | 0.55 | 0.50 | 0.80 | 0.82 |
| Normal vs. ES + EA + AS | 0.99 | 0.97 | 0.66 | 0.66 | 0.96 | 0.99 |

TABLE 4

| Criteria | P value for Assay | | | | | |
|---|---|---|---|---|---|---|
| | Assay 2 | Assay 4 | Assay 5 | Assay 6 | Assay 3 | Assay 1 |
| Alive vs. Dead | NS | NS | NS | NS | <0.05 | <0.05 |
| EA vs. AS | NS | NS | NS | NS | <0.05 | <0.05 |
| ES + EA vs. AS | <0.01 | <0.01 | NS | NS | <0.001 | <0.001 |
| ES vs. EA | NS | NS | NS | NS | NS | NS |
| SL + ES vs. EA + AS | <0.001 | 0.001 | NS | NS | <0.001 | <0.001 |
| SL vs. AS | <0.001 | <0.001 | NS | NS | <0.001 | <0.001 |
| SL vs. ES | <0.001 | <0.001 | NS | NS | <0.001 | <0.001 |
| SL vs. ES + EA | <0.001 | <0.001 | NS | NS | <0.001 | <0.001 |
| SL vs. ES + EA + AS | <0.001 | <0.001 | NS | NS | <0.001 | <0.001 |
| Normal vs. ES + EA + AS | <0.001 | 0.001 | <0.01 | <0.01 | <0.001 | <0.001 |

The following conclusions were drawn from these data:

(1) The truncated form-specific assays that exclude splice variant have no discriminatory power in this patient population;

(2) The "total" CCL23 assay that recognizes CCL23, CCL23 splice variant, and possible truncated forms perform comparable to the "full length" CCL23 assay that recognizes CCL23 and CCL23 splice variant, but not the truncated forms in a paired comparison; and (3) The CCL23 splice variant assay performs comparably to the total CCL23 assay that recognizes CCL23 and CCL23 splice variant, but not the truncated forms in a paired comparison while the CCL23-specific assay that does not recognize the CCL23 splice variant also performs comparably to the total CCL23 assay that recognizes CCL23 and CCL23 splice variant.

Given the relative performance of assays 1, 2, and 3, odds ratios were calculated to demonstrate the relative performance of these assays to distinguish subjects at risk to progress to the more severe sepsis categories. The following data presents odds rations for the relative risk of falling into the following two groups: Outcome 0: patients enrolled in the study with low risk infection (or no infection) and with 2 or more SIRS criteria upon presentation to the ED; outcome 1: patients with a high risk infection and 2 or more SIRS criteria, but not meeting the criteria for severe sepsis, or septic shock within 72 hrs of presentation to the ED, or patients that did not meet the criteria for severe sepsis, or septic shock upon presentation to the ED, but advanced to meet these criteria within 72 hrs, or patients meeting the criteria for severe sepsis, or septic shock upon presentation to the ED. In Table 5, N is the number of patients whose samples were analyzed within each group, odds ratios are calculated relative to the first quartile, 95% LCI is the lower 95% confidence interval of each odds ratio, and 95% UCI is the upper 95% confidence interval of each odds ratio.

TABLE 5

| | Quartiles | | | |
|---|---|---|---|---|
| | 1st | 2nd | 3rd | 4th |
| Assay 1 | | | | |
| N (Outcome 0) | 49 | 35 | 13 | 7 |
| N (Outcome 1) | 16 | 30 | 51 | 58 |
| Total N | 65 | 65 | 64 | 65 |
| Odds Ratio | 1.00 | 2.63 | 12.01 | 25.38 |
| 95% LCI | n/a | 1.25 | 5.24 | 9.66 |
| 95% UCI | n/a | 5.53 | 27.56 | 66.68 |
| CCL23 concentration at lower interval boundary (ng/mL) | n/a | 3.88 | 6.14 | 10.25 |
| Assay 2 | | | | |
| N (Outcome 0) | 47 | 34 | 12 | 11 |
| N (Outcome 1) | 18 | 31 | 52 | 54 |
| Total N | 65 | 65 | 64 | 65 |
| Odds Ratio | 1.00 | 2.38 | 11.31 | 12.82 |
| 95% LCI | n/a | 1.15 | 4.93 | 5.50 |
| 95% UCI | n/a | 4.94 | 25.95 | 29.87 |
| CCL23 concentration at lower interval boundary (ng/mL) | n/a | 1.46 | 3.07 | 5.53 |
| Assay 3 | | | | |
| N (Outcome 0) | 47 | 36 | 14 | 7 |
| N (Outcome 1) | 18 | 29 | 50 | 58 |
| Total N | 65 | 65 | 64 | 65 |
| Odds Ratio | 1.00 | 2.10 | 9.33 | 21.63 |
| 95% LCI | n/a | 1.01 | 4.17 | 8.33 |
| 95% UCI | n/a | 4.37 | 20.84 | 56.17 |
| CCL23 concentration at lower interval boundary (ng/mL) | n/a | 0.29 | 0.48 | 0.80 |

While all three of these assays perform acceptably, Assay 1, which is the total CCL23 assay that recognizes CCL23, CCL23 splice variant, and possible truncated forms, may be superior, although there are not enough patient samples to demonstrate the statistical significance of this observation.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of" the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method of formulating a CCL23 immunoassay for use in assessing a subject with SIRS, comprising:

providing an antibody pair for use in a sandwich format immunoassay, wherein said antibody pair is selected from the group consisting of:

(1) a first and a second antibody, each of which binds to an epitope common to both CCL23 and CCL23 splice variant;

(2) a first antibody that binds to the portion of CCL23 missing N-terminal processed forms of CCL23 selected from the group consisting of $CCL23_{19-99}$, $CCL23_{22-99}$, $CCL23_{27-99}$, and $CCL23_{30-99}$, and a second antibody that binds to an epitope common to both CCL23 and CCL23 splice variant;

(3) a first antibody that binds to CCL23 splice variant but not CCL23, and a second antibody that binds to an epitope common to both CCL23 and CCL23 splice variant; and (4) a first and a second antibody, each of which binds to CCL23 splice variant but not CCL23;

measuring a sample obtained from a subject having SIRS using said antibody pair in a sandwich format immunoassay; and assessing said subject having SIRS based on said measuring.

2. The method according to claim 1, wherein at least one of said first and second antibodies binds to an epitope common to both CCL23 and CCL23 splice variant that is C-terminal to the splice variant insertion MLWRRKIGPQMTLSHAAG (SEQ ID NO:3).

3. The method according to claim 1, wherein each of said first and second antibodies binds to an epitope common to both CCL23 and CCL23 splice variant, and each of said first and second antibodies binds one or more of N-terminal processed forms of CCL23 selected from the group consisting of $CCL23_{19-99}$, $CCL23_{22-99}$, $CCL23_{27-99}$, and $CCL23_{30-99}$.

4. The method according to claim 1, wherein one of said first or second antibodies is conjugated to a solid phase, and the other of said first or second antibodies is conjugated to a detectable label.

* * * * *